(12) United States Patent
Hong et al.

(10) Patent No.: US 12,098,239 B2
(45) Date of Patent: Sep. 24, 2024

(54) MODIFIED EPOXY RESIN IMMOBILIZED ENZYME, PREPARATION METHOD THEREFOR AND APPLICATION THEREOF

(71) Applicant: ASYMCHEM LIFE SCIENCE (TIANJIN) CO., LTD., Tianjin (CN)

(72) Inventors: Hao Hong, Morrisville, NC (US); Gage James, Morrisville, NC (US); Yi Xiao, Tianjin (CN); Vyasarayani Williams Rajasekar, Tianjin (CN); Yuxia Cui, Tianjin (CN); Na Zhang, Tianjin (CN); Jiadong Zhao, Tianjin (CN); Yanyan Gao, Tianjin (CN)

(73) Assignee: ASYMCHEM LIFE SCIENCE (TIANJIN) CO., LTD., Tianjin (CN)

( * ) Notice: Subject to any disclaimer, the term of this patent is extended or adjusted under 35 U.S.C. 154(b) by 17 days.

(21) Appl. No.: 17/758,746

(22) PCT Filed: Jan. 14, 2020

(86) PCT No.: PCT/CN2020/072009
§ 371 (c)(1),
(2) Date: Jul. 13, 2022

(87) PCT Pub. No.: WO2021/142618
PCT Pub. Date: Jul. 22, 2021

(65) Prior Publication Data
US 2023/0104206 A1 Apr. 6, 2023

(51) Int. Cl.
*C08G 59/14* (2006.01)
*C08G 59/16* (2006.01)
*C08G 59/42* (2006.01)
*C12N 11/08* (2020.01)
*C12N 11/089* (2020.01)

(52) U.S. Cl.
CPC ..... *C08G 59/1438* (2013.01); *C08G 59/1477* (2013.01); *C12N 11/089* (2020.01)

(58) Field of Classification Search
None
See application file for complete search history.

(56) References Cited

U.S. PATENT DOCUMENTS

2009/0093032 A1 4/2009 Tagliani

FOREIGN PATENT DOCUMENTS

| CN | 101974510 | | 2/2011 |
| CN | 103224926 | | 7/2013 |
| CN | 105219745 | | 1/2016 |
| CN | 105219745 | A * | 1/2016 |
| CN | 105624128 | | 6/2016 |
| CN | 110352179 | | 10/2019 |

OTHER PUBLICATIONS

Lopez et al., "Preparation of a robust biocatalyst of d-amino acid oxidase on sepabeads supports using the glutaraldehyde crosslinking method," Enzyme and Microbial Technology, vol. 37, pp. 750-756 (Year: 2005).*
Ke et al., 2018, "Recent advances in enzyme immobilization", Chinese Journal of Biotechnology, 34:188-203.
Reis et al., 2019, "Design of Immobilized Enzyme Biocatalysts: Drawbacks and Opportunities", Quim. Nova, 42:768-783.
Zhang et al., 2018, "Immobilization of L-glutamate oxidase by ES-105 epoxy resin", Chinese Journal of Bioprocess Engineering, 16:30-35.
European Extended Search Report for 20914725.5, Issued May 23, 2024, 15 pages.
Linqiu, C., et al., "Carrier-immobilized enzymes: principles, applications and design, Adsorption-based Immobilization," Carrier-Bound Immobilized ENzymes: Principles, Applications and Design, 2005, pp. 53-168.
Mateo, C., et al., "Preparation of a very stable immobilized Solanum tuberosum epoxide hydrolase," Tetrahedron: Asymmetry, vol. 18 (2007), pp. 1233-1238.
Abian et al: "Preparation of artificial hyper-hydrophilic microenvironments (polymeric salts) surrounding enzyme molecules New enzyme derivatives to be used in any reaction medium", Journal of Molecular Catalysis B: Enzymatic, vol. 19, 2002, pp. 295-303, XP085629433, ISSN: 1381-1177, DOI: 10.1016/S1381-1177(02)00180-7.
Alonso N et al: "Immobilization and stabilization of glutaryl acylase on aminated sepabeads supports by the glutaraldehyde crosslinking method", Journal of Molecular Catalysis B: Enzymatic, vol. 35, No. 1-3, Aug. 2005 (Aug. 2005), pp. 57-61, XP027658822, ISSN: 1381-1177 [retrieved on Aug. 1, 2005].
Drozd et al: "Functionalized Magnetic Bacterial Cellulose Beads as Carrier for Lecitase Ultra Immobilization", Applied Biochemistry and Biotechnology, Humana Press Inc, New York, vol. 187, No. 1, Jun. 18, 2018 (Jun. 18, 2018) , pp. 176-193, XP036672128, ISSN: 0273-2289, DOI: 10.1007/S12010-018-2816-1 [retrieved on Jun. 18, 2018].
Kumaraguru et al: "Immobilization of Lecitase ultra on recyclable polymer support: application in resolution oftrans-methyl (4-methoxyphenyl)glycidate in organic solvents", Tetrahedron Asymmetry, Pergamon Press Ltd, Oxford, GB, vol. 28, No. 11, Nov. 3, 2017 (Nov. 3, 2017), pp. 1612-1617, XP085293685, ISSN: 0957-4166, DOI: 10.1016/J.TETASY.2017.10.006.

(Continued)

*Primary Examiner* — Randy P Gulakowski
*Assistant Examiner* — Ha S Nguyen
(74) *Attorney, Agent, or Firm* — Riverside Law LLP

(57) ABSTRACT

Disclosed are a modified epoxy resin immobilized enzyme, a preparation method therefor and an application thereof. Herein, the preparation method includes the following steps: modifying an epoxy resin, adding a polyethyleneimine to a modified epoxy resin for further modification, and then adding an enzyme to be immobilized and a glutaraldehyde for immobilization, to obtain the modified epoxy resin immobilized enzyme. The epoxy resin is modified, the polyethyleneimine is added to the modified epoxy resin for the further modification, and an aldehyde group in the resin and an amino group in the polyethyleneimine are covalently bound to each enzyme, then it is activated by the bifunctional reagent glutaraldehyde.

20 Claims, No Drawings
Specification includes a Sequence Listing.

(56) References Cited

OTHER PUBLICATIONS

Mateo, C., et al. "Advances in the design of new epoxy supports for enzyme immobilization-stabilization." Biochemical society transactions 35.6 (2007): 1593-1601.
Partial Supplementary European Search Report issued in App. No. EP20914725, dated Feb. 14, 2024, 14 pages.
Virgen-Ortiz et al. "Polyethylenimine: a very useful ionic polymer in the design of immobilized enzyme biocatalysts." Journal of materials chemistry B 5.36 (2017): 7461-7490.
Zhou et al. "Synchronized purification and immobilization of his-tagged B-glucosidase via Fe304/PMG core/shell magnetic nanoparticles." Scientific Reports 7.1 (2017): 41741.

* cited by examiner

SEQUENCE LISTING

```
<160> NUMBER OF SEQ ID NOS: 5

<210> SEQ ID NO 1
<211> LENGTH: 459
<212> TYPE: PRT
<213> ORGANISM: Chromobacterium violaceum DSM30191

<400> SEQUENCE: 1

Met Gln Lys Gln Arg Thr Thr Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Ser Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
    130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190
```

Lys Asp Met Thr Pro Asp Glu Phe Gly Val Ala Ala Arg Trp Leu
            195                 200                 205

Glu Glu Lys Ile Leu Glu Ile Gly Ala Asp Lys Val Ala Ala Phe Val
210                 215                 220

Gly Glu Pro Ile Gln Gly Ala Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
            275                 280                 285

Gly Leu Ser Ser Gly Tyr Leu Pro Ile Gly Ala Val Phe Val Gly Lys
            290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
            355                 360                 365

His Val Asp Asp Val Arg Gly Val Gly Met Val Gln Ala Phe Thr Leu
            370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Arg
                405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
            435                 440                 445

Phe Glu Gln Thr Leu Lys Ala Arg Gly Leu Ala
            450                 455

<210> SEQ ID NO 2
<211> LENGTH: 476
<212> TYPE: PRT
<213> ORGANISM: Arthrobacter citreus

<400> SEQUENCE: 2

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
                20                  25                  30

Pro Val Pro Ile Glu Ser Thr Glu Gly Asp Tyr Leu Ile Thr Pro Gly
            35                  40                  45

Gly Thr Arg Leu Leu Asp Phe Phe Asn Gln Leu Cys Cys Val Asn Leu
        50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro

```
                100                 105                 110
Gly Lys Val Arg Phe Val Ser Thr Gly Ser Glu Ala Val Glu Thr Ala
            115                 120                 125

Leu Asn Ile Ala Arg Leu Tyr Thr Asn Arg Pro Leu Val Thr Arg
130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Cys Ser Ser Ala Val Leu Met Ala
            180                 185                 190

Pro Ser Ser Asn Thr Phe Gln Asp Ser Asn Gly Asn Tyr Leu Lys Asp
            195                 200                 205

Glu Asn Gly Glu Leu Leu Ser Val Lys Tyr Thr Arg Arg Met Ile Glu
        210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Val Pro Gln Ile Arg
                245                 250                 255

Lys Met Thr Lys Glu Leu Gly Val Leu Trp Ile Ser Asp Glu Val Leu
            260                 265                 270

Thr Gly Phe Gly Arg Thr Gly Lys Trp Phe Gly Tyr Gln His Tyr Gly
            275                 280                 285

Val Gln Pro Asp Ile Ile Thr Met Gly Lys Gly Leu Ser Ser Ser Ser
        290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
            355                 360                 365

Glu Leu Leu Gln Glu Lys His Lys Ser Ile Gly Asn Phe Asp Gly Tyr
        370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
            435                 440                 445

Val Ser Arg Gly Asp Ile Asp Lys Ala Met Asp Ala Leu Asp Tyr Ala
        450                 455                 460

Leu Asp Tyr Leu Glu Ser Gly Glu Trp Gln Gln Ser
465                 470                 475

<210> SEQ ID NO 3
<211> LENGTH: 253
<212> TYPE: PRT
<213> ORGANISM: Acetobacter sp. CCTCC M209061

<400> SEQUENCE: 3
```

```
Met Ala Arg Val Ala Gly Lys Val Ala Ile Val Ser Gly Ala Ala Asn
1               5                   10                  15
Gly Ile Gly Lys Ala Thr Ala Gln Leu Leu Ala Lys Glu Gly Ala Lys
            20                  25                  30
Val Val Ile Gly Asp Leu Lys Glu Glu Asp Gly Gln Lys Ala Val Ala
        35                  40                  45
Glu Ile Lys Ala Ala Gly Gly Glu Ala Ala Phe Val Lys Leu Asn Val
50                  55                  60
Thr Asp Glu Ala Ala Trp Lys Ala Ala Ile Gly Gln Thr Leu Lys Leu
65                  70                  75                  80
Tyr Gly Arg Leu Asp Ile Ala Val Asn Asn Ala Gly Ile Asn Tyr Ser
            85                  90                  95
Gly Ser Val Glu Ser Thr Ser Leu Glu Asp Trp Arg Arg Val Gln Ser
            100                 105                 110
Ile Asn Leu Asp Gly Val Phe Leu Gly Thr Gln Val Ala Ile Glu Ala
            115                 120                 125
Met Lys Lys Ser Gly Gly Gly Ser Ile Val Asn Leu Ser Ser Ile Ser
        130                 135                 140
Gly Leu Ile Gly Asp Pro Met Leu Ala Ala Tyr Val Ala Ser Lys Gly
145                 150                 155                 160
Gly Val Arg Leu Phe Thr Lys Ser Ala Ala Leu His Cys Ala Lys Ser
            165                 170                 175
Gly Tyr Lys Ile Arg Val Asn Ser Val His Pro Gly Tyr Ile Trp Thr
            180                 185                 190
Pro Met Val Ala Gly Leu Thr Lys Glu Asp Ala Ala Arg Gln Lys
            195                 200                 205
Leu Val Asp Leu His Pro Ile Gly His Leu Gly Glu Pro Asn Asp Ile
        210                 215                 220
Ala Tyr Gly Ile Leu Tyr Leu Ala Ser Asp Glu Ser Lys Phe Val Thr
225                 230                 235                 240
Gly Ser Glu Leu Val Ile Asp Gly Gly Tyr Thr Ala Gln
            245                 250

<210> SEQ ID NO 4
<211> LENGTH: 541
<212> TYPE: PRT
<213> ORGANISM: Rhodococcus sp. Phi1

<400> SEQUENCE: 4

Met Thr Ala Gln Ile Ser Pro Thr Val Asp Ala Val Ile Gly
1               5                   10                  15
Ala Gly Phe Gly Gly Ile Tyr Ala Val His Lys Leu His Asn Glu Gln
            20                  25                  30
Gly Leu Thr Val Val Gly Phe Asp Lys Ala Asp Gly Pro Gly Gly Thr
        35                  40                  45
Trp Tyr Trp Asn Arg Tyr Pro Gly Ala Leu Ser Asp Thr Glu Ser His
50                  55                  60
Leu Tyr Arg Phe Ser Phe Asp Arg Asp Leu Leu Gln Asp Gly Thr Trp
65                  70                  75                  80
Lys Thr Thr Tyr Ile Thr Gln Pro Glu Ile Leu Glu Tyr Leu Glu Ser
            85                  90                  95
Val Val Asp Arg Phe Asp Leu Arg Arg His Phe Arg Phe Gly Thr Glu
            100                 105                 110
Val Thr Ser Ala Ile Tyr Leu Glu Asp Glu Asn Leu Trp Glu Val Ser
            115                 120                 125
```

```
Thr Asp Lys Gly Glu Val Tyr Arg Ala Lys Tyr Val Asn Ala Val
130                 135                 140
Gly Leu Leu Ser Ala Ile Asn Phe Pro Asp Leu Pro Gly Leu Asp Thr
145                 150                 155                 160
Phe Glu Gly Glu Thr Ile His Thr Ala Ala Trp Pro Glu Gly Lys Asn
                165                 170                 175
Leu Ala Gly Lys Arg Val Gly Val Ile Gly Thr Gly Ser Thr Gly Gln
                180                 185                 190
Gln Val Ile Thr Ala Leu Ala Pro Glu Val Glu His Leu Thr Val Phe
        195                 200                 205
Val Arg Thr Pro Gln Tyr Ser Val Pro Val Gly Asn Arg Pro Val Thr
210                 215                 220
Lys Glu Gln Ile Asp Ala Ile Lys Ala Asp Tyr Asp Gly Ile Trp Asp
225                 230                 235                 240
Ser Val Lys Lys Ser Ala Val Ala Phe Gly Phe Glu Glu Ser Thr Leu
                245                 250                 255
Pro Ala Met Ser Val Ser Glu Glu Arg Asn Arg Ile Phe Gln Glu
                260                 265                 270
Ala Trp Asp His Gly Gly Phe Arg Phe Met Phe Gly Thr Phe Gly
        275                 280                 285
Asp Ile Ala Thr Asp Glu Ala Ala Asn Glu Ala Ala Ala Ser Phe Ile
290                 295                 300
Arg Ser Lys Ile Ala Glu Ile Ile Glu Asp Pro Glu Thr Ala Arg Lys
305                 310                 315                 320
Leu Met Pro Thr Gly Leu Tyr Ala Lys Arg Pro Leu Cys Asp Asn Gly
                325                 330                 335
Tyr Tyr Glu Val Tyr Asn Arg Pro Asn Val Glu Ala Val Ala Ile Lys
                340                 345                 350
Glu Asn Pro Ile Arg Glu Val Thr Ala Lys Gly Val Val Thr Glu Asp
        355                 360                 365
Gly Val Leu His Glu Leu Asp Val Leu Val Phe Ala Thr Gly Phe Asp
370                 375                 380
Ala Val Asp Gly Asn Tyr Arg Arg Ile Glu Ile Arg Gly Arg Asn Gly
385                 390                 395                 400
Leu His Ile Asn Asp His Trp Asp Gly Gln Pro Thr Ser Tyr Leu Gly
                405                 410                 415
Val Thr Thr Ala Asn Phe Pro Asn Trp Phe Met Val Leu Gly Pro Asn
                420                 425                 430
Gly Pro Phe Thr Asn Leu Pro Pro Ser Ile Glu Thr Gln Val Glu Trp
        435                 440                 445
Ile Ser Asp Thr Val Ala Tyr Ala Glu Arg Asn Glu Ile Arg Ala Ile
450                 455                 460
Glu Pro Thr Pro Glu Ala Glu Glu Trp Thr Gln Thr Cys Thr Asp
465                 470                 475                 480
Ile Ala Asn Ala Thr Leu Phe Thr Arg Gly Asp Ser Trp Ile Phe Gly
                485                 490                 495
Ala Asn Val Pro Gly Lys Lys Pro Ser Val Leu Phe Tyr Leu Gly Gly
                500                 505                 510
Leu Gly Asn Tyr Arg Asn Val Leu Ala Gly Val Val Ala Asp Ser Tyr
        515                 520                 525
Arg Gly Phe Glu Leu Lys Ser Ala Val Pro Val Thr Ala
530                 535                 540
```

<210> SEQ ID NO 5
<211> LENGTH: 603
<212> TYPE: PRT
<213> ORGANISM: Rhodococcus ruber-SD1

<400> SEQUENCE: 5

```
Met Thr Thr Ser Ile Asp Arg Glu Ala Leu Arg Arg Lys Tyr Ala Glu
1               5                   10                  15

Glu Arg Asp Lys Arg Ile Arg Pro Asp Gly Asn Asp Gln Tyr Ile Arg
            20                  25                  30

Leu Asp His Val Asp Gly Trp Ser His Asp Pro Tyr Met Pro Ile Thr
        35                  40                  45

Pro Arg Glu Pro Lys Leu Asp His Val Thr Phe Ala Phe Ile Gly Gly
    50                  55                  60

Gly Phe Ser Gly Leu Val Thr Ala Ala Arg Leu Arg Glu Ser Gly Val
65                  70                  75                  80

Glu Ser Val Arg Ile Ile Asp Lys Ala Gly Asp Phe Gly Gly Val Trp
                85                  90                  95

Tyr Trp Asn Arg Tyr Pro Gly Ala Met Cys Asp Thr Ala Ala Met Val
            100                 105                 110

Tyr Met Pro Leu Leu Glu Glu Thr Gly Tyr Met Pro Thr Glu Lys Tyr
        115                 120                 125

Ala His Gly Pro Glu Ile Leu Glu His Cys Gln Arg Ile Gly Lys His
    130                 135                 140

Tyr Asp Leu Tyr Asp Asp Ala Leu Phe His Thr Glu Val Thr Asp Leu
145                 150                 155                 160

Val Trp Gln Glu His Asp Gln Arg Trp Arg Ile Ser Thr Asn Arg Gly
                165                 170                 175

Asp His Phe Thr Ala Gln Phe Val Gly Met Gly Thr Gly Pro Leu His
            180                 185                 190

Val Ala Gln Leu Pro Gly Ile Pro Gly Ile Glu Ser Phe Arg Gly Lys
        195                 200                 205

Ser Phe His Thr Ser Arg Trp Asp Tyr Asp Tyr Thr Gly Gly Asp Ala
    210                 215                 220

Leu Gly Ala Pro Met Asp Lys Leu Ala Asp Lys Arg Val Ala Val Ile
225                 230                 235                 240

Gly Thr Gly Ala Thr Ala Val Gln Cys Val Pro Glu Leu Ala Lys Tyr
                245                 250                 255

Cys Arg Glu Leu Tyr Val Val Gln Arg Thr Pro Ser Ala Val Asp Glu
            260                 265                 270

Arg Gly Asn His Pro Ile Asp Glu Lys Trp Phe Ala Gln Ile Ala Thr
        275                 280                 285

Pro Gly Trp Gln Lys Arg Trp Leu Asp Ser Phe Thr Ala Ile Trp Asp
    290                 295                 300

Gly Val Leu Thr Asp Pro Ser Glu Leu Ala Ile Glu His Glu Asp Leu
305                 310                 315                 320

Val Gln Asp Gly Trp Thr Ala Leu Gly Gln Arg Met Arg Ala Ala Val
                325                 330                 335

Gly Ser Val Pro Ile Glu Gln Tyr Ser Pro Glu Asn Val Gln Arg Ala
            340                 345                 350

Leu Glu Glu Ala Asp Asp Glu Gln Met Glu Arg Ile Arg Ala Arg Val
        355                 360                 365

Asp Glu Ile Val Thr Asp Pro Ala Thr Ala Ala Gln Leu Lys Ala Trp
    370                 375                 380
```

```
Phe Arg Gln Met Cys Lys Arg Pro Cys Phe His Asp Asp Tyr Leu Pro
385                 390                 395                 400

Ala Phe Asn Arg Pro Asn Thr His Leu Val Asp Thr Gly Gly Lys Gly
                405                 410                 415

Val Glu Arg Ile Thr Glu Asn Gly Val Val Val Ala Gly Val Glu Tyr
            420                 425                 430

Glu Val Asp Cys Ile Val Tyr Ala Ser Gly Phe Glu Phe Leu Gly Thr
            435                 440                 445

Gly Tyr Thr Asp Arg Ala Gly Phe Asp Pro Thr Gly Arg Asp Gly Val
        450                 455                 460

Lys Leu Ser Glu His Trp Ala Gln Gly Thr Arg Thr Leu His Gly Met
465                 470                 475                 480

His Thr Tyr Gly Phe Pro Asn Leu Phe Val Leu Gln Leu Met Gln Gly
                485                 490                 495

Ala Ala Leu Gly Ser Asn Ile Pro His Asn Phe Val Glu Ala Ala Arg
            500                 505                 510

Val Val Ala Ala Ile Val Asp His Val Leu Ser Thr Gly Thr Ser Ser
        515                 520                 525

Val Glu Thr Thr Lys Glu Ala Glu Gln Ala Trp Val Gln Leu Leu Leu
    530                 535                 540

Asp His Gly Arg Pro Leu Gly Asn Pro Glu Cys Thr Pro Gly Tyr Tyr
545                 550                 555                 560

Asn Asn Glu Gly Lys Pro Ala Glu Leu Lys Asp Arg Leu Asn Val Gly
                565                 570                 575

Tyr Pro Ala Gly Ser Ala Ala Phe Phe Arg Met Met Asp His Trp Leu
            580                 585                 590

Ala Ala Gly Ser Phe Asp Gly Leu Thr Phe Arg
            595                 600
```

MODIFIED EPOXY RESIN IMMOBILIZED ENZYME, PREPARATION METHOD THEREFOR AND APPLICATION THEREOF

CROSS-REFERENCE TO RELATED APPLICATIONS

This application is a U.S. national phase application filed under 35 U.S.C. § 371 claiming benefit to International Patent Application No. PCT/CN2020/072009, filed on Jan. 14, 2020, the disclosure of which is incorporated by reference herein in its entirety.

SEQUENCE LISTING

The present application contains a Sequence Listing, which has been submitted electronically in ASCII format and is hereby incorporated by reference in its entirety. Said ASCII copy is named "206418_0014_00 US_Sequence_Listing_ST25.txt" and is 20,748 bytes in size. Except for changes to the bibliographic information and this Sequence Listing is identical to an ASCII formatted sequence listing of the international application No. PCT/CN2020/072009 filed on Jan. 14, 2020. The sequence listing submitted via EFS-Web is part of the specification and is herein incorporated by reference in its entirety.

TECHNICAL FIELD

The present disclosure relates to the technical field of biocatalysis, in particular to a modified epoxy resin immobilized enzyme, a preparation method therefor and an application thereof.

BACKGROUND

Enzymes are biocatalysts widely used in different industrial processes because of their high activity, selectivity, and specificity compared to chemical catalysts. Enzymes are able to produce complex compounds under very mild reaction conditions, allowing to develop more sustainable processes and this attribute has made the enzymatic processes as emerging platform. Because of the biological origins of enzymes, they generally have operational characteristics that differ from those required for an industrial process.

The biocatalysts can be produced using whole living or dead cells or the crude enzyme or purified enzymes depending on the type and application of enzyme. The expanded pool of enzymes and advances in protein engineering has made it possible to produce economically viable biocatalyst on a commercial scale.

The increasing use of enzymes as catalysts in industrial processes has led to increasing demand of enzymes in immobilized form, as it offers unique process and cost advantages. The immobilized enzymes frequently termed as "biocatalysts" are widely used for industrial organic synthesis and biotransformation.

One of the most useful strategies to successfully use enzymes in biotechnological processes is their immobilization. A proper enzyme immobilization is a powerful tool to improve enzymatic properties, such as resistance to drastic reaction conditions (e.g., pH and temperature far from their physiological range), enhanced enzyme activity, multiple reusability or continuous use, and improvement of substrate specificity and enantiomer specificity, or product selectivity.

The emergence of novel immobilization platforms is enabling a seamless integration of immobilized enzymes in continuous flow bio-catalysis. The discovery and evolution of new and highly efficient enzymes, novel retrosynthetic approaches with an emphasis on biocatalysis, reduced cost of recombinant proteins and enzyme immobilization strategies all combine to augur well for flow biocatalysis.

The immobilization methods are based on the distinctive characteristics of functional groups of the amino acid side chains of the enzymes, which interact to (or react with) the support in several ways. The enzymes can be attached on the support surface by adsorption via reversible bonds, like van der Waals forces, hydrophobic, or ionic linkages, or by irreversible chemical bonds, such as covalent attachment (Sheldon et al 2013).

The covalent attachment provides an irreversible binding of the biocatalyst to the support and, for this reason, it prevents enzyme leakage and in effect enhancing the enzyme recyclability. Among covalent supports, Epoxy-activated supports are almost-ideal matrixes to perform a very easy immobilization of proteins on both a laboratory and industrial scale (Hannibal-Friedrich et al 1980; Hernaiz et al 2000; Calleri et al 2004; Podgornik, H. et al 2002). These supports are directly supplied in an activated form. Moreover, they are very stable during storage and transport even suspended in neutral aqueous media. Moreover, it is possible to carry out longterm immobilizations, permitting us to fully cover the support surface with the enzyme. Furthermore, epoxy-activated supports react with proteins under very mild experimental conditions (e.g. pH 7.0), promoting very small chemical modifications of the protein (secondary amine, thioether and ether).

Generally speaking, the soluble proteins are scarcely reactive with epoxy groups at neutral pH values. This low reactivity of epoxy supports causes the immobilization of enzymes on these supports to be produced via a two-step mechanism: first, a rapid and mild physical adsorption of the protein on the support is produced; secondly, a covalent reaction between the adsorbed protein and neighboring epoxide groups occurs [Wheatley et al 1999; Bauer-Arnaz et al 1998].

Due to this mechanism, commercial epoxy supports utilized to immobilize proteins are fairly hydrophobic, in order to adsorb proteins when they are incubated at high ionic strength (by a hydrophobic interaction). In some cases, the use of hydrophobic supports can promote the wrong folding of the protein structure caused by the stabilization of anomalous structures with internal hydrophobic amino acids located in the outer layer (Fitzpatrick P A et al 1993). Moreover, quite often the use of high salt concentrations can deactivate the activity of different enzymes especially of multimeric ones where the linkage among subunits is promoted by ionic forces (Fernandez-Lafuente et al 2009). Albeit the fact that epoxy supports are quite an important platform for immobilization, with the emerging new enzymes, especially more evolved multimeric enzymes, an overall improved and novel process of immobilization on epoxy supports are warranted.

Bolivar et al (2007) evaluated different immobilization strategies for the immobilization of Formate dehydrogenase from *Candida boidinii* using epoxy, amino-epoxy, glyoxyl (epoxy) or treatment of enzymes adsorbed on aminated supports with glutaraldehyde. The best results in terms of stability were achieved using amino-epoxy supports (by a 12-fold factor compared to soluble enzyme) and glyoxyl agarose supports (by a 150-fold factor). However, both cases activity recovery was just over 15% in addition to poor and identical stability with soluble enzyme.

Truppo et al (2012) evaluated the use of several polymer-based resins (SEPABEADS) from Mitsubishi for the immobilization of Januvia transaminase (CDX0117, Codexis) for the purpose of using the immobilized enzyme in organic solvents. The resins selected included three epoxide functionalized supports for covalent immobilization (EC-EP, EC-HFA/S, and EXE119), and two adsorption supports for immobilization through hydrophobic interaction (EXA252 and EXE120). Though many supports tested showed activity, SEPABEAD EXE120, (adsorption support) a highly hydrophobic octadecyl functionalized polymethacrylate resin, provided the highest specific activity (FIG. 1). As much as 45% of the enzyme activity charged to the immobilization process was recovered on the EXE120 resin, resulting in a 4 wt % loading of transaminase on the resin (40 mg transaminase per 1 g solid support). Under the immobilized conditions, the epoxy support EC-EP showed poor enzyme binding and expression, which may be due to denaturation of enzyme by the epoxy support.

Hui Ren et al (2016) reported immobilization of thermophilic esterase AFEST from the archaeon *Archaeoglobus fulgidus* epoxy support Sepabeads EC-EP via covalent attachment, and the immobilized enzyme was then employed as a biocatalyst for poly("-caprolactone) synthesis. The enzyme loading and recovered activity of immobilized enzyme was measured to be 72 mg/g and 10.4 U/mg using p-nitrophenyl caprylate as the substrate at 80° C., respectively. The immobilized enzyme good reusability, with monomer conversion values exceeding 75% during 15 batch reactions.

Ana I. Benitez-Mateos et al (2018) reported the use of porous carriers for the development of self-sufficient immobilized transaminase by binding along with the cofactor, PLP. In this work, w-transaminase from *Halomonas elongata* was co-immobilized with PLP onto porous methacrylate-based metal chelated carriers coated with polyethyleneimine. The packed-bed reactor continuously run up to 50 column volumes at 1.45 mL×min−1 in the enantioselective deamination of model amines (α-methylbenzyl amine), yielding >90% conversion in all cycles without exogenous addition of cofactor. Similar approach was made with transaminases from *Chromobacterium violaceum* and *Pseudomonas fluorescens* which showed similar activity. However, overall the maximum operating time the stability of enzyme reports is 133 minutes, despite the fact this approach seemed positive.

Despite several publications, there are following limitations on these methods, particularly in relation with the enzymes listed in Table 1.

TABLE 1

| Short name | Enzyme | Source |
| --- | --- | --- |
| TA-Af | Transaminase | *Aspergillus fumigatus* |
| TA-Ac | Transaminase | *Arthrobacter citreus* |
| TA-Cv | Transaminase | *Chromobacterium violaceum* DSM30191 |
| KRED-Ac | Ketoreductase | *Acetobacter sp.* CCTCC M209061 |
| KRED-Cm | Ketoreductase | *Candida macedoniensis.* AKU4588 |
| CHMO-Bp | Cyclohexanone monooxygenase | *Brachymonas petroleovorans* |
| CHMO-Rr | Cyclohexanone monooxygenase | *Rhodococcus ruber*-SD1 |
| CHMO-Rs | Cyclohexanone monooxygenase | *Rhodococcus sp.* Phi1 |
| ERED-Sc | Ene reductase | *Saccharomyces cerevisiae* |
| ERED-Chr | Ene reductase | *ChrySEQbacterium sp.* CA49 |
| NIT-An | Nitrilase | *Aspergillus niger* CBS 513.88 |

TABLE 1-continued

| Short name | Enzyme | Source |
| --- | --- | --- |
| NIT-Nc | Nitrilase | *Neurospora crassa* OR74A |
| IRED-Str | Imine reductase | *Streptomyces* sp. |
| IRED-Bc | Imine reductase | *Bacillus cereus* |
| PAL-An | Ammonia lyase | *photorhabdus luminescens* |
| PAL-Ss | Ammonia lyase | *Solenostemon scutellarioides* |
| AADH-Bc | Amino acid dehydrogenase | *Bacillus cereus* |
| AADH-Bs | Amino acid dehydrogenase | *Bacillus sphaericus* |
| FDH | Ammonium formate dehydrogenase | *Candida boidini* |

Methods of the immobilized enzymes reported in an existing technology are not suitable for industrial applications of the enzymes in Table 1, and its stability needs to be further improved.

SUMMARY

The present disclosure aims to provide a modified epoxy resin immobilized enzyme, a preparation method therefor and an application thereof, as to improve the recycling stability of enzymes.

In order to achieve the above purpose, according to one aspect of the present disclosure, a preparation method for a modified epoxy resin immobilized enzyme is provided. The preparation method includes the following steps: modifying an epoxy resin, adding a polyethyleneimine to a modified epoxy resin for further modification, and then adding an enzyme to be immobilized and a glutaraldehyde for immobilization, to obtain the modified epoxy resin immobilized enzyme.

Further, the step of modifying the epoxy resin includes using a sodium periodate to oxidize the epoxy resin or using an iminodiacetic acid to react with the epoxy resin.

Further, while the step of modifying the epoxy resin is to use the sodium periodate to oxidize the epoxy resin, before the sodium periodate is added, an acetic acid is firstly used to treat the epoxy resin, and after the enzyme to be immobilized and the glutaraldehyde are added for immobilization, it further includes a step of adding a cross-linking agent glutaraldehyde or dextran aldehyde for secondary cross-linking.

Further, while the step of modifying the epoxy resin is to use the iminodiacetic acid to react with the epoxy resin, after the polyethyleneimine is added to the modified epoxy resin for further modification, it further includes a step of adding metal ion solution for treatment, and the enzyme to be immobilized has a his tag; preferably, the metal ion solution is selected from one or more of a cobalt chloride, a cobalt sulfate, a nickel chloride, a copper sulfate, a ferrous chloride or a ferrous sulfate; preferably, the concentration of the metal ion solution is 5~100 mmol/L, preferably 10~50 mmol/L.

Further, the adding sequence of the enzyme to be immobilized and the glutaraldehyde is the enzyme to be immobilized and the glutaraldehyde, or the glutaraldehyde and the enzyme to be immobilized.

Further, in the step of adding the polyethyleneimine to the modified epoxy resin for further modification, it further includes adding a cofactor, and the cofactor is a nicotinamide adenine dinucleotide (NAD+), a nicotinamide adenine dinucleotide phosphate (NADP+) or a pyridoxal phosphate (PLP); preferably, the polyethyleneimine participates in the reaction in the form of polyethyleneimine aqueous solution, and the final concentration of the cofactor in the polyethyleneimine aqueous solution is 1~10 mg/mL, preferably 3~6 mg/mL; and preferably, before the cross-linking agent glutaraldehyde or dextran aldehyde is used, it further comprises a step of modifying the cross-linking agent with a polyethylene glycol (PEG), and the PEG modification of the cross-linking agent glutaraldehyde or dextran aldehyde includes dissolving the cross-linking agent with water, adding the PEG, and stirring at 20~30° C. for 1~6 h, herein the PEG is selected from PEG400~PEG2000, and the mass ratio of PEG to the cross-linking agent is 1:1~10:1, further preferably 2:1~4:1.

Further, in the step of treating the epoxy resin with the acetic acid, the acetic acid used is acetic acid solution, and the concentration of the acetic acid in the acetic acid solution is 0.5~3 M, preferably 1~2 M; and the volume-to-mass ratio of the acetic acid solution to the epoxy resin is 5~20:1, preferably 10~15:1; preferably, in the step of oxidizing the epoxy resin with the sodium periodate, the concentration of the sodium periodate in sodium periodate solution used is 50~500 mM, preferably 100~200 mM; and the volume-to-mass ratio of the sodium periodate solution to the epoxy resin is 5~20:1, preferably 5~15:1; preferably, the molecular weight of the polyethyleneimine is 3 KDa~70 KDa, and the concentration of the polyethyleneimine aqueous solution is 0.5%~3%, preferably 1%~2%; and pH of the polyethyleneimine aqueous solution is 6~11, further preferably 7~10; preferably, the volume/mass final concentration of the cross-linking agent glutaraldehyde or dextran aldehyde is 0.1%~3%, preferably 0.3%~2%; preferably, the mass ratio of the enzyme to the modified epoxy resin is 0.05~0.3:1; and preferably, in the step of using the iminodiacetic acid to react with the epoxy resin, the iminodiacetic acid used is iminodiacetic acid aqueous solution, the concentration of the iminodiacetic acid aqueous solution is 0.5~3 M, preferably 1~2 M, and the volume-to-mass ratio of the iminodiacetic acid aqueous solution to the epoxy resin is 5~20:1, preferably 10~15:1; and pH of the iminodiacetic acid aqueous solution is 6.0~10.0, preferably 7.0~9.0.

Further, the treatment time after the acetic acid is mixed with the epoxy resin is 6~24 h, preferably 10~15 h; preferably, the reaction time after the sodium periodate solution is mixed with the epoxy resin is 1~6 h, preferably 2~3 h; preferably, the reaction time after the polyethyleneimine aqueous solution is mixed with the epoxy resin is 1~20 h, preferably 3~6 h; preferably, the reaction time after the enzyme is mixed with the modified epoxy resin is 2~24 h, preferably 15~20 h; preferably, after the cross-linking agent is added, the reaction time is 10~120 min, preferably 20~60 min; preferably, the action time after the iminodiacetic acid aqueous solution is mixed with the epoxy resin is 0.5~6 h, preferably 1~2 h; and preferably, the action time after the polyethyleneimine aqueous solution is mixed with a support is 1~20 h, further, it is 3~6 h; after the metal containing solution are added, the action time is 1~6 h, further, it is 1~3 h; and the action time after the enzyme solution is mixed with the support is 4~48 h, and further, the action time is 15~20 h.

Further, the epoxy resin is selected from one or more in a group consisting of Purolite®Lifetech™ECR8285, ECR8204, ECR8209, SEPLITE®LX1000EA, LX1000EP, LX103B, EP200, LX1000HFA, HFA001, LX107S, LX1000SW, LX1000SD, HECHENG®ES1, ES103, ES105, ES108 or ES109.

Further, the enzyme to be immobilized is selected from one or more in a group consisting of a transaminase derived from *Chromobacterium violaceum* DSM30191, a transaminase derived from *Aspergillus fumigatus*, a transaminase derived from *Vibrio fluvialis* strain JS17, a ketoreductase derived from *Acetobacter* sp. CCTCC M209061, a ketoreductase derived from *Candida macedoniensis* AKU4588, a cyclohexanone monooxygenase derived from *Rhodococcus* sp. Phi1, a cyclohexanone monooxygenase derived from *Brachymonas petroleovorans*, a monooxygenase derived from *Rhodococcus ruber*-SD1, an ammonia lyase derived from *Photorhabdus luminescens*, an ammonia lyase derived from *Solenostemon scutellarioides*, an Ene reductase derived from *Saccharomyces cerevisiae*, an Ene reductase derived from ChrySEQbacterium sp. CA49, an imine reductase derived from *Streptomyces* sp or *Bacillus cereus*, a leucine dehydrogenase derived from *Bacillus cereus*, a phenylalanine dehydrogenase derived from *Bacillus sphaericus*, a nitrilase derived from *Aspergillus niger* CBS 513.88 and a nitrilase derived from *Neurospora crassa* OR74A; and the transaminase derived from *Chromobacterium violaceum* DSM30191 is a mutant having a sequence of SEQ ID NO: 2 or SEQ ID NO: 3; the transaminase derived from *Arthrobacter citreus* is a mutant having a sequence of SEQ ID NO: 5 or SEQ ID NO: 6; the ketoreductase derived from *Acetobacter* sp. CCTCC M209061 is a mutant having a sequence of SEQ ID NO: 8 or SEQ ID NO: 9; the cyclohexanone monooxygenase derived from *Rhodococcus* sp. Phi1 is a mutant having a sequence of SEQ ID NO: 11 or SEQ ID NO: 12; and the cyclohexanone monooxygenase derived from *Rhodococcus ruber*-SD1 is a mutant having a sequence of SEQ ID NO: 14 or SEQ ID NO: 15.

According to another aspect of the present disclosure, a modified epoxy resin immobilized enzyme is provided. The immobilized enzyme is prepared by any one of the above preparation methods.

According to another aspect of the present disclosure, an application of the modified epoxy resin immobilized enzyme in an aqueous buffer reaction system or an organic solvent reaction system is provided.

Further, the aqueous buffer reaction system or the organic solvent reaction system is reacted in a packed bed reactor or a continuous stirred tank reactor.

By applying the technical scheme of the present disclosure, the epoxy resin is modified, the polyethyleneimine is added to the modified epoxy resin for the further modification, and an aldehyde group in the resin and an amino group in the polyethyleneimine are covalently bound to each enzyme, then it is activated by the bifunctional reagent glutaraldehyde. In this way, a steric resin arm is increased, to form a network structure, it may be more easily bound to the enzyme by covalent binding, and the enzyme load may also be improved because the steric inhibition is reduced.

DETAILED DESCRIPTION OF THE EMBODIMENTS

It should be noted that embodiments in the present application and features of the embodiments may be combined with each other in the case without conflicting. The present disclosure is described in detail below in combination with the embodiments.

EXPLANATION OF TERMS AND ABBREVIATIONS

IDA: Iminodiacetic acid disodium salt hydrate.
GA: Glutaraldehyde
PEI: Polyethyleneimine
PEG: Polyethylene glycol In most cases, biocatalysis can rely on efficient biological catalysts. Enzymes are versatile biological catalysts with high stereoselectivity and regioselectivity and a high turnover rate. However, free enzymes are relatively sensitive and unstable, and they cannot be recovered and reused efficiently. To overcome these limitations and broaden their applicability, before use, free enzymes are usually attached to an inert, insoluble material via immobilization.

Epoxy resins have been used in immobilization of several kinds of enzymes like lipase, acylases, the process is very simple and easy to handle, but enzyme should be purified before immobilization to get positive activity recovery, and activity recovery is still not as good as other immobilization protocols even pure enzyme is used. In view of this, the present application proposes the following technical solution.

According to a typical embodiment of the present disclosure, a preparation method for a modified epoxy resin immobilized enzyme is provided. The preparation method includes the following steps: modifying an epoxy resin, adding a polyethyleneimine to a modified epoxy resin for further modification, and then adding an enzyme to be immobilized and a glutaraldehyde for immobilization, to obtain the modified epoxy resin immobilized enzyme.

By applying the technical scheme of the present disclosure, the epoxy resin is modified, the polyethyleneimine is added to the modified epoxy resin for the further modification, and an aldehyde group in the resin and an amino group in the polyethyleneimine are covalently bound to each enzyme, then it is activated by the bifunctional reagent glutaraldehyde. In this way, a steric resin arm is increased, to form a network structure, it may be more easily bound to the enzyme by covalent binding, and the enzyme load may also be improved because the steric inhibition is reduced.

In a typical embodiment of the present disclosure, the step of modifying the epoxy resin includes using a sodium periodate to oxidize the epoxy resin or using an iminodiacetic acid to react with the epoxy resin, as to obtain the epoxy resin with the improved performance. Preferably, while the step of modifying the epoxy resin is to use the sodium periodate to oxidize the epoxy resin, before the sodium periodate is added, an acetic acid is firstly used to treat the epoxy resin, and after the enzyme to be immobilized and the glutaraldehyde are added for immobilization, it further includes a step of adding a cross-linking agent glutaraldehyde or dextran aldehyde for secondary cross-linking, so that the immobilization is stronger.

In the present application, the modification of the epoxy resin with iminodiacetic acid and metal is modified. After the epoxy resin is reacted with the iminodiacetic acid, PEI is added and bound to the resin by ionic attachment, and then it is treated with the suitable metal. After that, a His-tagged enzyme is added, and then glutaraldehyde cross-linking is performed so that the attachment is stronger. PEI may bind to the metal stronger than the iminodiacetic acid, and may also cross-link with the glutaraldehyde, so that the enzyme leakage is much reduced. According to a typical embodiment of the present disclosure, while the step of modifying the epoxy resin is to use the iminodiacetic acid to react with the epoxy resin, after the polyethyleneimine is added to the modified epoxy resin for further modification, it further includes a step of adding metal ion solution for treatment, and the enzyme to be immobilized has a his tag; preferably, the metal ion solution is selected from one or more of a cobalt chloride, a cobalt sulfate, a nickel chloride, a copper sulfate, a ferrous chloride or a ferrous sulfate; and preferably, the concentration of the metal ion solution is 5~100 mmol/L, preferably 10~50 mmol/L.

Preferably, the adding sequence of the enzyme to be immobilized and the glutaraldehyde is the enzyme to be immobilized and the glutaraldehyde, or the glutaraldehyde and the enzyme to be immobilized successively.

According to a typical embodiment of the present disclosure, in the step of adding the polyethyleneimine to the modified epoxy resin for further modification, it further includes adding a cofactor, and the cofactor is NAD+, NADP+ or PLP; preferably, the polyethyleneimine participates in the reaction in the form of polyethyleneimine aqueous solution, and the final concentration of the cofactor in the polyethyleneimine aqueous solution is 1~10 mg/mL, preferably 3~6 mg/mL; and preferably, before the cross-linking agent glutaraldehyde or dextran aldehyde is used, it further comprises a step of modifying the cross-linking agent with PEG, and the PEG modification of the cross-linking agent glutaraldehyde or dextran aldehyde includes dissolving the cross-linking agent with water, adding the PEG, and stirring at 20~30° C. for 1~6 h, herein the PEG is selected from PEG400~PEG2000, and the mass ratio of PEG to the cross-linking agent is 1:1~10:1, the reusability is good, and further preferably it is 2:1~4:1.

According to a typical embodiment of the present disclosure, in the step of treating the epoxy resin with the acetic acid, the acetic acid used is acetic acid solution, and the concentration of the acetic acid in the acetic acid solution is 0.5~3 M, preferably 1~2 M; and the volume-to-mass ratio of the acetic acid solution to the epoxy resin is 5~20:1, preferably 10~15:1; preferably, in the step of oxidizing the epoxy resin with the sodium periodate, the concentration of the sodium periodate in sodium periodate solution used is 50~500 mM, preferably 100~200 mM; and the volume-to-mass ratio of the sodium periodate solution to the epoxy resin is 5~20:1, preferably 5~15:1; preferably, the molecular weight of the polyethyleneimine is 3 KDa~70 KDa, and the concentration of the polyethyleneimine aqueous solution is 0.5%~3%, preferably 1%~2%; and pH of the polyethyleneimine aqueous solution is 6~11, further preferably 7~10; preferably, the volume/mass final concentration of the cross-linking agent glutaraldehyde or dextran aldehyde is 0.1%~3%, preferably 0.3%~2%; preferably, the mass ratio of the enzyme to the modified epoxy resin is 0.05~0.3:1; and preferably, in the step of using the iminodiacetic acid to react with the epoxy resin, the iminodiacetic acid used is iminodiacetic acid aqueous solution, the concentration of the iminodiacetic acid aqueous solution is 0.5~3 M, preferably 1~2 M, and the volume-to-mass ratio of the iminodiacetic acid aqueous solution to the epoxy resin is 5~20:1, preferably 10~15:1; and pH of the iminodiacetic acid aqueous solution is 6.0~10.0, preferably 7.0~9.0, the stability is best.

According to a typical embodiment of the present disclosure, the treatment time after the acetic acid is mixed with the epoxy resin is 6~24 h, preferably 10~15 h; preferably, the reaction time after the sodium periodate solution is mixed with the epoxy resin is 1~6 h, preferably 2~3 h; preferably, the reaction time after the polyethyleneimine aqueous solution is mixed with the epoxy resin is 1~20 h, preferably 3~6 h; preferably, the reaction time after the enzyme is mixed with the modified epoxy resin is 2~24 h, preferably 15~20 h; preferably, after the cross-linking agent is added, the reaction time is 10~120 min, preferably 20~60 min; preferably, the action time after the iminodiacetic acid aqueous solution is mixed with the epoxy resin is 0.5~6 h, preferably 1~2 h; and preferably, the action time after the polyethyleneimine aqueous solution is mixed with a support is 1~20 h, further, it is 3~6 h; after the metal containing solution are added, the action time is 1~6 h, further, it is 1~3 h; and the action time after the enzyme solution is mixed with the support is 4~48 h, and further, the action time is 15~20 h.

According to a typical embodiment of the present disclosure, the epoxy resin is selected from one or more in a group consisting of Purolite®Lifetech™ECR8285, ECR8204, ECR8209, SEPLITE®LX1000EA, LX1000EP, LX103B, EP200, LX1000HFA, HFA001, LX107S, LX1000SW, LX1000SD, HECHENG®ES1, ES103, ES105, ES108 or ES109.

According to a typical embodiment of the present disclosure, the enzyme to be immobilized is selected from one or more in a group consisting of a transaminase derived from *Chromobacterium violaceum* DSM30191, a transaminase derived from *Aspergillus fumigatus*, a transaminase derived from *Vibrio fluvialis* strain JSI7, a ketoreductase derived from *Acetobacter* sp. CCTCC M209061, a ketoreductase derived from *Candida macedoniensis* AKU4588, a cyclohexanone monooxygenase derived from *Rhodococcus* sp. Phi1, a cyclohexanone monooxygenase derived from *Brachymonas petroleovorans*, a monooxygenase derived from *Rhodococcus ruber*-SD1, an ammonia lyase derived from *photorhabdus luminescens*, an ammonia lyase derived from *Solenostemon scutellarioides*, an Ene reductase derived from *Saccharomyces cerevisiae*, an Ene reductase derived from ChrySEQbacterium sp. CA49, an imine reductase derived from *Streptomyces* sp or *Bacillus cereus*, a leucine dehydrogenase derived from *Bacillus cereus*, a phenylalanine dehydrogenase derived from *Bacillus sphaericus*, a nitrilase derived from *Aspergillus niger* CBS 513.88 and a nitrilase derived from *Neurospora crassa* OR74A; and the transaminase derived from *Chromobacterium violaceum* DSM30191 is a mutant having a sequence of SEQ ID NO: 2 or SEQ ID NO: 3; the transaminase derived from *Arthrobacter citreus* is a mutant having a sequence of SEQ ID NO: 5 or SEQ ID NO: 6; the ketoreductase derived from *Acetobacter* sp. CCTCC M209061 is a mutant having a sequence of SEQ ID NO: 8 or SEQ ID NO: 9; the cyclohexanone monooxygenase derived from *Rhodococcus* sp. Phi1 is a mutant having a sequence of SEQ ID NO: 11 or SEQ ID NO: 12; and the cyclohexanone monooxygenase derived from *Rhodococcus ruber*-SD1 is a mutant having a sequence of SEQ ID NO: 14 or SEQ ID NO: 15.

The chemical processes involved in the reactions of the above enzymes is briefly described as follows:

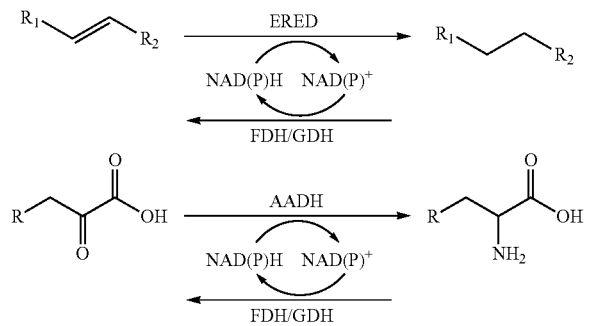

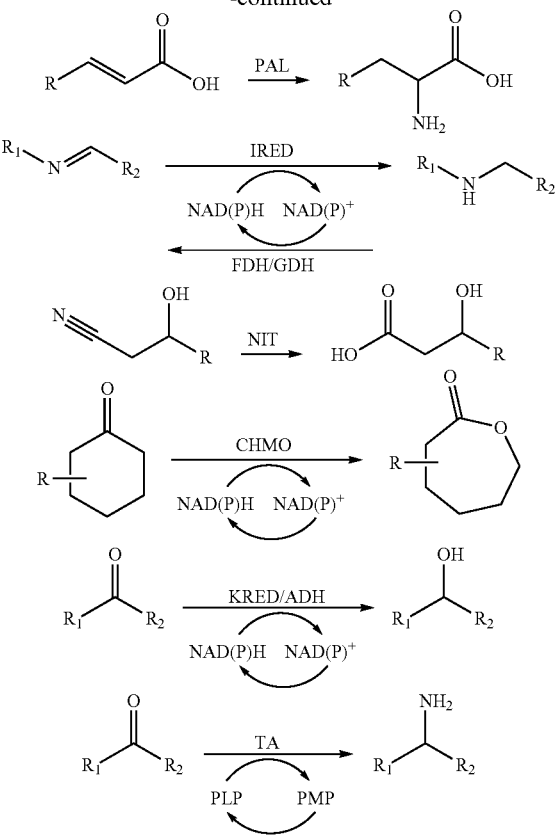

$R$, $R_1$ and $R_2$ in the above reaction formulas may be each independently selected from H, a substituted or unsubstituted alkyl, a substituted or unsubstituted cycloalkyl, a substituted or unsubstituted aralkyl, a substituted or unsubstituted heterocyclyl, a substituted or unsubstituted heterocycloalkyl, or a fused ring system formed by $R_1$ and its linked heterocycle.

According to a typical embodiment of the present disclosure, a modified epoxy resin immobilized enzyme is provided. The immobilized enzyme is prepared by any one of the above preparation methods.

According to a typical embodiment of the present disclosure, an application of the modified epoxy resin immobilized enzyme in an aqueous buffer reaction system or an organic solvent reaction system is provided. Preferably, the aqueous buffer reaction system or the organic solvent reaction system is reacted in a packed bed reactor or a continuous stirred tank reactor.

In a typical embodiment of the present disclosure, the epoxy resins (for example, the epoxy resins shown in Table 2, herein Epoxy is an epoxy group) are modified, thereby the reusability of the epoxy resin immobilized enzyme is improved.

TABLE 2

| Resin name | Resin functional group |
|---|---|
| ECR8285 | Epoxy/C4 |
| ECR8204 | Epoxy |
| ECR8209 | Epoxy |
| LX1000EA | Epoxy |
| LX1000EP | Epoxy |
| EP200 | Epoxy |

TABLE 2-continued

| Resin name | Resin functional group |
|---|---|
| LX1000HFA | Amino-Epoxy |
| HFA001 | Amino-Epoxy |
| LX103B | Epoxy |
| LX107S | Epoxy |
| LX1000SW | Epoxy |
| LX1000SD | Epoxy |
| ES1 | Epoxy |
| ES103 | Epoxy |
| ES105 | Epoxy |
| ES108 | Epoxy |
| ES109 | Epoxy |

Typically, the properties of the epoxy resins are changed by oxidizing the epoxy resins with the sodium periodate or modifying the epoxy resins with the iminodiacetic acid. The specific description is as follows:

I. Immobilization of Enzymes on Sodium Periodate Oxidized Epoxy Resins

After oxidation by sodium periodate, oxidized epoxy resins were further modified by PEI or PEI along with cofactors for each enzyme accordingly through covalent binding between aldehyde group in resin and amino group in PEI, followed by activation by bifunctional reagent glutaraldehyde, through this way, space arm of resin increased and net structure formed, and enzyme can be combined much easier by covalent binding because of reduced steric inhibition, and enzyme loading could also be improved. To make immobilization stronger, extra linker like glutaraldehyde or dextran aldehyde was added for secondary cross-linking.

Enzyme also can be combined on PEI modified oxidized epoxy resin by ionic adsorption primarily, followed by adding glutaraldehyde to perform crosslinking between enzyme, PEI and resin to form net structure and strong combination.

II. Immobilization of Enzymes on Iminodiacetic Modified Epoxy Resins

It is previously reported to immobilize the His-tagged enzyme on the metal-modified epoxy resin. The epoxy resin was first reacted with iminodiacetic acid to convert part of the epoxides on the surface of the beads and then treated with a suitable metal ion solution for the complexation on the resin. His-tagged enzyme was then added and a selective interaction between the poly-histidine tag and the metal allowed for a quick complexation, followed by a reaction between nucleophilic residues on the protein surface (Lys, Cys, or Ser) and the unreacted epoxy residues on the beads to give a successful along with covalent immobilization. The metal ion was then removed by washing with an EDTA solution. To ensure that no reactive epoxide remained, the beads were finally treated with glycine as capping agent. Main enzyme can be specifically bound onto resin, but stability was still not very good, after 6 cycles, less than 10% residual activity left. Complexation of metal and iminodiacetic acid modified resin was not strong enough, and enzyme can be easily leaked out.

In the present application, modification of epoxy by iminodiacetic acid and metal was revised. After reaction with iminodiacetic acid, PEI was added and combined with resin by ionic attachment, and then treated with suitable metal. Then His-tagged enzyme was added, and followed by glutaraldehyde crosslinking to make the attachment stronger. PEI can bind metal stronger than iminodiacetic acid, along with cross linking by glutaraldehyde, made enzyme leaking out reduce a lot.

To make the technical solution suitable for enzymes without His-tag, metal was not used after PEI modification, glutaraldehyde was added and form covalent binding with PEI and residual hydroxyl residual on surface of epoxy resin, then enzyme was added and bounded with covalent attachment.

In both methods, Enzyme also can be added before glutaraldehyde addition, and ionic adsorbed primarily with PEI and affinity adsorption, followed by adding glutaraldehyde to perform crosslinking between enzyme, PEI and resin to form net structure and strong combination.

The beneficial effects of the present disclosure are further described below in combination with the embodiments.

The enzymes used in the following embodiments and its sources are shown in Tables 3~8 below.

TABLE 3

| Enzyme | Short name | Species origin |
|---|---|---|
| D-amino acid transaminase | TA-Bt | B. thuringiensis |
| Pyruvate aminotransferase | TA-Vf | Vibrio fluvialis strain JS17 |
| Ketoreductase | KRED-Ss | Sporobolomyces salmonicolor |
|  | KRED-Cm | Candida macedoniensis. AKU4588 |
| Alcohol dehydrogenase | ADH-Tb | Thermoanaerobium brockii |
| D-lactate dehydrogenase | D-LDH | Lactobacillus helveticus |
| Ammonium formate dehydrogenase | FDH | Candida boidinii |
| Glucose 1-dehydrogenase | GDH | Lysinibacillus sphaericus G10 |
| Cyclohexanone monooxygenase | CHMO-Rs | Rhodococcus sp. Phi1 |
|  | CHMO-Bp | Brachymonas petroleovorans |
|  | CHMO-Rr | Rhodococcus ruber-SD1 |
| Ene reductase | ERED-Sc | Saccharomyces cerevisiae |
|  | ERED-Chr | ChrySEQbacterium sp. CA49 |
| Imine reductase | IRED-Str | Streptomyces sp. |
|  | IRED-Bc | Bacillus cereus |
| Leucine dehydrogenase | AADH-Bc | Bacillus cereus |
| Phenylalanine dehydrogenase | AADH-Bs | Bacillus sphaericus |

TABLE 4

| TA-Cv | Sequence number | Sequence |
|---|---|---|
| Female parent | SEQ ID NO: 1 | MQKQRTTSQWRELDAAHHLHPFTDTASLNQAGARVMTR GEGVYLWDSEGNKIIDGMAGLWCVNVGYGRKDFAEAARR QMEELPFYNTFFKTTHPAVVELSSLLAEVTPAGFDRVFYTN SGSESVDTMIRMVRRYWDVQGKPEKKTLIGRWNGYHGS TIGGASLGGMKYMHEQGDLPIPGMAHIEQPWWYKHGKD MTPDEFGVVAARWLEEKILEIGADKVAAFVGEPIQGAGGVI VPPATYWPEIERICRKYDVLLVADEVICGFGRTGEWFGHQ HFGFQPDLFTAAKGLSSGYLPIGAVFVGKRVAEGLIAGGDF NHGFTYSGHPVCAAVAHANVAALRDEGIVQRVKDDIGPYM |

TABLE 4-continued

| TA-Cv | Sequence number | Sequence |
|---|---|---|
| | | QKRWRETFSRFEHVDDVRGVGMVQAFTLVKNKAKRELFP DFGEIGTLCRDIFFRNNLIMRACGDHIVSAPPLVMTRAEVD EMLAVAERCLEEFEQTLKARGLA |
| Mutant 1 (TA-Cv-V1) | SEQ ID NO: 2 | R416T + T7C + S47C + Q380L |
| Mutant 2 (TA-Cv-V2) | SEQ ID NO: 3 | R416T + T7C + S47C + R405E + K90G + A95P + 304D + Q380L + I297L |

TABLE 5

| TA-Ac | Sequence number | Sequence |
|---|---|---|
| Female parent | SEQ ID NO: 4 | MGLTVQKINWEQVKEWDRKYLMRTFSTQNEYQPVPIESTE GDYLITPGGTRLLDFFNQLCCVNLGQKNQKVNAAIKEALDRY GFVWDTYATDYKAKAAKIIIEDILGDEDWPGKVRFVSTGSEA VETALNIARLYTNRPLVVTREHDYHGWTGGAATVTRLRSFRS GLVGENSESFSAQIPGSSCSSAVLMAPSSNTFQDSNGNYLK DENGELLSVKYTRRMIENYGPEQVAAVITEVSQGVGSTMPP YEYVPQIRKMTKELGVLWISDEVLTGFGRTGKWFGYQHYGV QPDIITMGKGLSSSSLPAGAVVVSKEIAAFMDKHRWESVSTY AGHPVAMAAVCANLEVMMEENLVEQAKNSGEYIRSKLELLQ EKHKSIGNFDGYGLLWIVDIVNAKTKTPYVKLDRNFRHGMNP NQIPTQIIMEKALEKGVLIGGAMPNTMRIGASLNVSRGDIDKA MDALDYALDYLESGEWQQS |
| Mutant 1 (TA-Ac-V1) | SEQ ID NO: 5 | L3S + V5S + C60Y + F164L + A178L + S187A + I180V + L370A + G411D + S186G + Y384F + I389F + V252I + L404Q + E171D |
| Mutant 2 (TA-Ac-V2) | SEQ ID NO: 6 | L3S + V5S + C60Y + F164L + A178L + S187A + I180V + L370A + G411D + S186G + Y384F + I389F + V252I + E424Q + M423K |

TABLE 6

| KRED-Ac | Sequence number | Sequence |
|---|---|---|
| Female parent | SEQ ID NO: 7 | MARVAGKVAIVSGAANGIGKATAQLLAK EGAKVVIGDLKEEDGQKAVAEIKAAGGE AAFVKLNVTDEAAWKAAIGQTLKLYGRL DIAVNNAGINYSGSVESTSLEDWRRVQS INLDGVFLGTQVAIEAMKKSGGGSIVNL SSISGLIGDPMLAAYVASKGGVRLFTKS AALHCAKSGYKIRVNSVHPGYIWTPMVA GLTKEDAAARQKLVDLHPIGHLGEPNDI AYGILYLASDESKFVTGSELVIDGGYTAQ |
| Mutant 1 (KRED-Ac-V1) | SEQ ID NO: 8 | E144S + A94N + N156V |
| Mutant 2 (KRED-Ac-V2) | SEQ ID NO: 9 | E144S + A94T + N156T |

TABLE 7

| CHMO-Rs | Sequence number | Sequence |
|---|---|---|
| Female parent | SEQ ID NO: 10 | MTAQISPTVVDAVVIGAGFGGIYAVHKLHNEQGLTVVGFDK ADGPGGTWYWNRYPGALSDTESHLYRFSFDRDLLQDGTW KTTYITQPEILEYLESVVDRFDLRRHFRFGTEVTSAIYLEDEN LWEVSTDKGEVYRAKYVVNAVGLLSAINFPDLPGLDTFEGE TIHTAAWPEGKNLAGKRVGVIGTGSTGQQVITALAPEVEHLT VFVRTPQYSVPVGNRPVTKEQIDAIKADYDGIWDSVKKSAV AFGFEESTLPAMSVSEEERNRIFQEAWDHGGGFRFMFGTF GDIATDEAANEAAASFIRSKIAEIIEDPETARKLMPTGLYAKR PLCDNGYYEVYNRPNVEAVAIKENPIREVTAKGVVTEDGVL HELDVLVFATGFDAVDGNYRRIEIRGRNGLHINDHWDGQPT |

TABLE 7-continued

| CHMO-Rs | Sequence number | Sequence |
|---|---|---|
| | | SYLGVTTANFPNWFMVLGPNGPFTNLPPSIETQVEWISDTV AYAERNEIRAIEPTPEAEEEWTQTCTDIANATLFTRGDSWIF GANVPGKKPSVLFYLGGLGNYRNVLAGVVADSYRGFELKS AVPVTA |
| Mutant 1 (CHMO-Rs-Cv-V1) | SEQ ID NO: 11 | F508Y + F435N + L438A + T436S + F280V + S441V |
| Mutant 2 (CHMO-Rs-V2) | SEQ ID NO: 12 | F508Y + F435N + L438A + T436S + F280V + S441V + L510V |

TABLE 8

| CHMO-Rr | Sequence number | Sequence |
|---|---|---|
| Female parent | SEQ ID NO: 13 | MTTSIDREALRRKYAEERDKRIRPDGNDQYIRLDHVDGWS HDPYMPITPREPKLDHVTFAFIGGGFSGLVTAARLRESGVE SVRIIDKAGDFGGVWYWNRYPGAMCDTAAMVYMPLLEET GYMPTEKYAHGPEILEHCQRIGKHYDLYDDALFHTEVTDLV WQEHDQRWRISTNRGDHFTAQFVGMGTGPLHVAQLPGIP GIESFRGKSFHTSRWDYDYTGGDALGAPMDKLADKRVAVI GTGATAVQCVPELAKYCRELYVVQRTPSAVDERGNHPIDEK WFAQIATPGWQKRWLDSFTAIWDGVLTDPSELAIEHEDLVQ DGWTALGQRMRAAVGSVPIEQYSPENVQRALEEADDEQM ERIRARVDEIVTDPATAAQLKAWFRQMCKRPCFHDDYLPAF NRPNTHLVDTGGKGVERITENGVVVAGVEYEVDCIVYASGF EFLGTGYTDRAGFDPTGRDGVKLSEHWAQGTRTLHGMHT YGFPNLFVLQLMQGAALGSNIPHNFVEAARVVAAIVDHVLS TGTSSVETTKEAEQAWVQLLLDHGRPLGNPECTPGYYNNE GKPAELKDRLNVGYPAGSAAFFRMMDHWLAAGSFDGLTFR |
| Mutant 1 (CHMO-Rr-V1) | SEQ ID NO: 14 | P190L + Y559M + C249V + C393V + C257A + M45T |
| Mutant 2 (CHMO-Rr-V2) | SEQ ID NO: 15 | Y559M + P190L + P504V |

Embodiment 1

Immobilization of Enzymes on Sodium Periodate Oxidized Epoxy Resins 5 g of an epoxy resin ECR8285 or LX1000EP is added to 20 mL of 1 M acetic acid respectively, it is mild stirred at a room temperature for 12 h, a support treated with the acetic acid is washed for 3 times with 20 mL of distilled water, and the treated support is suspended in 20 mL of 50 mM sodium periodate. It is mild stirred at the room temperature for 2 h, filtered and washed with the distilled water.

5 g of a modified epoxy resin is resuspended in 0.1 M phosphate buffer (PB), PEI is added, the final concentration is 1%, and pH is adjusted to pH 7.0. After being mild stirred for 2 h, 50-100 mM glutaraldehyde is added, and it is mild stirred at the room temperature for 1-2 h. Then the support resin is filtered and washed with 10 ml of water. The washed support is added to enzyme solution (10 ml of an enzyme, containing 5 mg/mL of a cofactor, dissolved in 40 mL of 100 mM PB, pH 7.0), it is stirred at 10-25° C. for 4 h, and overnights in a refrigerator. After standing overnight, the enzyme is filtered, and washed with 0.1 M PB (pH 7.0). Optionally, after standing overnight, excess glutaraldehyde (20-50 mM) or dextran aldehyde (10-50 mM) is added to solution, it is mild stirred for 1 h at 10-25° C., then filtered and washed with 0.1 M PB (pH 7.0).

Embodiment 2

Immobilization of enzymes on sodium periodate oxidized epoxy resins 5 g of epoxy beads are added to 50 mL of 1 M acetic acid, it is mild stirred at a room temperature for 12 h, a support treated with the acetic acid is washed for 3 times with 50 mL of distilled water, it is mild stirred for 10 minutes each time, and the treated support is suspended in 100 mL of a sodium periodate. It is mild stirred at the room temperature for 2 h, filtered and washed with the distilled water.

5 g of a modified epoxy resin is resuspended in 0.1 M PB, PEI is added, the final concentration is 1%, pH is adjusted to pH 7.0, and it is mild stirred for 2 h. Then the support is filtered and washed with 10 ml of water. The washed support is added to enzyme solution (10 ml of an enzyme, containing 5 mg/mL of a cofactor, dissolved in 40 mL of 100 mM PB, pH 7.0), it is stirred at the room temperature for 4 h, and overnights in a refrigerator. After standing overnight, 20-100 mM of a glutaraldehyde is added to solution, it is mild stirred at 10-25° C. for 1 h, then then filtered and washed with 0.1 M PB (pH 7.0).

Embodiment 3

Immobilization of Enzyme on Iminodiacetic Modified Epoxy Resin 4 g of a support is added to 8 mL of a support modification buffer (0.1 M sodium borate, 1 M iminodiacetic acid, pH 8.5), and it is shaken at a room temperature for 2 h. After 2 h, the support is filtered to remove the support modification buffer and washed with double distilled water, then resuspended with PB, and PEI is added so that the final concentration of PEI is 1%, pH is adjusted to 8.0-11.0, and it is mixed and mild stirred for 3 h. The support is filtered and washed for 3 times with 30 mL of water, then resuspended in 20 mL of PB, and metal containing solution are added, so that the concentration of the metal ions is 10-30 mM. The metal ions are selected from $CoCl_2$ or $NiCl_2.6H_2O$ or $CuSO_4.5H_2O$ or $FeCl_2$ or $FeCl_2$.

It is shaken for 2 h at the room temperature. The resin is rinsed again with the double distilled water and washed with 0.1 M PB (pH 8.0). It is resuspended again (pretreated with a cofactor according to each enzyme) in a buffer containing 50 mM glutaraldehyde (0.1 M PB pH=8.0), and mild stirred for 1 h at the room temperature. It is filtered and washed for 3 times with 0.1M PB (pH=7.0).

The pretreated resin is resuspended with 16 mL of 0.1 M PB (pH=7.0), 4-8 mL of enzyme solution (50-100 mg/mL of the protein content, and 3-10 mg/mL of the cofactor) is added, it is mild stirred for 30 minutes, and filtered after overnight. It is washed twice with 20 ml of 0.05 M PB (pH 7.5, it contains 0.05 M EDTA and 0.5 M NaCl), and mild stirred for 10 minutes each time. Subsequently, it is washed for 3 times with 20 ml of water, and then washed with 0.1 M PB (pH 7.5).

Embodiment 4

Immobilization of Enzyme on Iminodiacetic Modified Epoxy Resin 4 g of a support is added to 8 mL of a support modification buffer (0.1 M sodium borate, 1 M iminodiacetic acid, pH 8.5), and it is shaken at a room temperature for 2 h. After 2 h, the support is filtered to remove the support modification buffer and washed with double distilled water, then resuspended with PB, and PEI is added so that the final concentration of PEI is 1%, pH is adjusted to 8.0-11.0, and it is mixed and mild stirred for 3 h. The support is filtered and washed for 3 times with 30 mL of water, then resuspended in 20 mL of PB, and metal containing solution are added, so that the concentration of the metal ions is 10-30 mM. The metal ions are selected from $CoCl_2$ or $NiCl_2.6H_2O$ or $CuSO_4.5H_2O$ or $FeCl_2$ or $FeCl_2$.

It is shaken for 2 h at the room temperature. The resin is rinsed again with the double distilled water and washed with 0.1 M PB (pH 8.0). It is resuspended again with 16 mL of a buffer (0.1 M PB pH=8.0), 4-8 mL of enzyme solution (50-100 mg/mL of the protein content, and 3-10 mg/mL of the cofactor) is added, it is continuously mild stirred for 30 minutes, and filtered after overnight. It is washed twice with 20 ml of 0.05 M PB (pH 7.5, it contains 0.05 M EDTA and 0.5 M NaCl), and mild stirred for 10 minutes each time. Subsequently, it is washed for 3 times with 20 ml of water, and then washed with 0.1 M PB (pH 7.5).

Embodiment 5

Immobilization of Enzyme on Iminodiacetic Modified Epoxy Resin 4 g of a support is added to 8 mL of a support modification buffer (0.1 M sodium borate, 1 M iminodiacetic acid, pH 8.5), and it is shaken at a room temperature for 2 h. After 2 h, the support is filtered to remove the support modification buffer and washed with double distilled water, then resuspended with PB, and PEI is added so that the final concentration of PEI is 1%, pH is adjusted to 8.0-11.0, and it is suspended and mild stirred for 3 h. The support is filtered and washed for 3 times with 30 mL of water, then resuspended in 20 mL of PB, and metal containing solution are added, so that the concentration of the metal ions is 10-30 mM. The metal ions are selected from $CoCl_2$ or $NiCl_2.6H_2O$ or $CuSO_4.5H_2O$ or $FeCl_2$ or $FeCl_2$.

The support is filtered and washed for 3 times with 30 ml of water, and then resuspended in 16 mL of PB (0.1 M pH=8.0), 4-8 mL of enzyme solution (50-100 mg/mL of the protein content, and 3-10 mg/mL of the cofactor) is added, it is continuously mild stirred for 30 minutes, and filtered after overnight. 16 mL of 0.1 M PB (pH=8.0, 5 mg/ml of the cofactor and 50 mM glutaraldehyde) is added, and it is shaken gently for 30 minutes at the room temperature. It is washed twice with 20 ml of 0.05 M PB (pH 7.5, it contains 0.05 M EDTA and 0.5 M NaCl), and mild stirred for 10 minutes each time. Subsequently, it is washed for 3 times with 20 ml of water, and then washed with 0.1 M PB (pH 7.5).

Embodiment 6

Immobilization of Enzyme on Iminodiacetic Modified Epoxy Resin 4 g of a support is added to 8 mL of a support modification buffer (0.1 M sodium borate, 1 M iminodiacetic acid, pH 8.5), and it is shaken at a room temperature for 2 h. After 2 h, the support is filtered to remove the support modification buffer and washed with double distilled water, then resuspended with PB, and PEI is added so that the final concentration of PEI is 1%, pH is adjusted to 8.0-11.0, and it is mild stirred for 3 h. The support is filtered and washed for 3 times with 30 mL of water, then resuspended in 20 mL of PB, and metal containing solution are added, so that the concentration of the metal ions is 10-30 mM. The metal ions are selected from $CoCl_2$ or $NiCl_2.6H_2O$ Or $CuSO_4.5H_2O$ or $FeCl_2$ or $FeCl_2$.

The support is filtered and washed for 3 times with 30 ml of water, the pretreated support is resuspended in 16 mL of PB (0.1 M pH=8.0), 4-8 mL of enzyme solution (50-100 mg/mL of the protein content, and 3-10 mg/mL of the cofactor) is added, it is continuously mild stirred for 30 minutes, and filtered after overnight. 16 mL of 0.1 M PB (pH=8.0, 5 mg/ml of the cofactor and 50 mM glutaraldehyde) is added, and it is shaken gently for 30 minutes at the room temperature. It is washed twice with 20 ml of 0.05 M PB (pH 7.5, it contains 0.05 M EDTA and 0.5 M NaCl), and mild stirred for 10 minutes each time. Subsequently, it is washed for 3 times with 20 ml of water, and then washed with 0.1 M PB (pH 7.5).

Or the pretreated resin is resuspended with 16 mL of 0.1 M PB (pH=7.0), 4-8 mL of enzyme solution (50-100 mg/mL of the protein content, and 3-10 mg/mL of the cofactor) is added, it is mild stirred for 30 minutes, and filtered after overnight. It is washed twice with 20 ml of 0.05 M PB (pH 7.5, it contains 0.05 M EDTA and 0.5 M NaCl), and mild stirred for 10 minutes each time. Subsequently, it is washed for 3 times with 20 ml of water, and then washed with 0.1 M PB (pH 7.5).

Embodiment 7

As in Embodiment 2, the glutaraldehyde is changed to a PEI-modified glutaraldehyde, the molecular weight of PEG is 6000 Da, and the mass ratio of PEG to the glutaraldehyde is 1:1.

Embodiment 8

As in Embodiment 1, the glutaraldehyde is changed to aldehyde dextran.

Embodiment 9

As in Embodiment 5, the glutaraldehyde is changed to a PEI-modified glutaraldehyde, the molecular weight of PEG is 6000 Da, and the mass ratio of PEG to the glutaraldehyde is 1:1.

Embodiment 10

Conversion and reusability test of immobilized transaminase

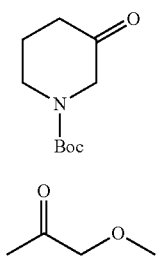

1

2

In a 10 mL reaction bulb, 0.3 mL of MeOH is added, 0.1 g of a main raw material 1 or a main raw material 2 is dissolved, 4 eq of isopropylamine hydrochloride and 1.0 mg of pyridoxal-5'-phosphate (PLP) are added, and 0.1 M PB 7.0 is supplemented until the final volume of reaction solution is 1 mL, then 5 mg of enzyme powder or cross-linked enzyme aggregate wet enzyme or cross-linked enzyme aggregate lyophilized powder prepared from 20 mg of the enzyme powder is added, and it is stirred at 30° C. for 16-20 h. The conversion rate in the system is detected by a high performance liquid chromatography (HPLC), and reaction data is shown in Table 9 below:

TABLE 9

| Enzyme | Support | Support modification material | Conversion (%) | Cycles |
|---|---|---|---|---|
| TA-Af | Free enzyme | –/– | >97 | 1 |
| | LX1000EP | No modification | <50 | 2 |
| | | IDA* | 75~80 | 4 |
| | | $IDA^1$ | 80 | 12 |
| | | $IDA^2$ | 80 | 14 |
| | | $IDA^3$ | 80 | 14 |
| | | $IDA^4$ | 80 | 16 |
| | | $SP^1$ | 80 | 8 |

TABLE 9-continued

| Enzyme | Support | Support modification material | Conversion (%) | Cycles |
|---|---|---|---|---|
| | | $SP^2$ | 80 | 11 |
| | | $SP^3$ | 80 | 7 |
| | | $SP^4$ | 80 | 9 |
| | ECR8285 | No modification | <60 | 3 |
| | | $IDA^1$ | 80 | 10 |
| | | $IDA^2$ | 90 | 16 |
| | | $IDA^3$ | 80 | 13 |
| | | $IDA^4$ | 80 | 11 |
| | | $SP^2$ | 80 | 13 |
| | | $SP^3$ | 80 | 14 |
| | ECR8204 | IDA* | 75 | 4 |
| | | $IDA^1$ | 80 | 7 |
| | | $IDA^2$ | 80 | 8 |
| | | $SP^2$ | 75 | 7 |
| | | $SP^3$ | 75 | 6 |
| | ECR8209 | IDA* | 70 | 4 |
| | | $IDA^1$ | 80 | 8 |
| | | $IDA^2$ | 80 | 8 |
| | | $IDA^4$ | 80 | 9 |
| | | $SP^2$ | 75 | 8 |
| | ES1 | IDA* | 75~80 | 5 |
| | | $IDA^1$ | 80 | 9 |
| | | $IDA^2$ | 80 | 9 |
| | | $IDA^4$ | 75 | 8 |
| | | $SP^2$ | 75 | 8 |
| | | $SP^3$ | 75 | 6 |
| | ES103 | IDA* | 70 | 3 |
| | | $IDA^1$ | 80 | 9 |
| | | $IDA^2$ | 80 | 8 |
| | | $IDA^4$ | 80 | 8 |
| | | $SP^2$ | 80 | 6 |
| | | $SP^3$ | 75 | 6 |
| TA-Ac | Free enzyme | –/– | >97 | 1 |
| | LX1000EP | No modification | 85 | 2 |
| | | IDA* | >97 | 4 |
| | | $IDA^1$ | >97 | 9 |
| | | $IDA^2$ | >97 | 8 |
| | | $IDA^4$ | >97 | 8 |
| | | $SP^2$ | >97 | 9 |
| | | $SP^3$ | >97 | 7 |
| | ECR8285 | IDA* | 85 | 3 |
| | | $IDA^1$ | >97 | 7 |
| | | $IDA^2$ | >97 | 11 |
| | | $IDA^4$ | >97 | 13 |
| | | $SP^2$ | >97 | 13 |
| | | $SP^3$ | >97 | 15 |
| | ES1 | IDA* | 80 | 4 |
| | | $IDA^1$ | >97 | 6 |
| | | $IDA^2$ | >97 | 13 |
| | | $IDA^4$ | >97 | 14 |
| | | $SP^2$ | >97 | 12 |
| | | $SP^3$ | >97 | 14 |
| TA-Ac-V1 | ECR8285 | $IDA^2$ | >97 | 19 |
| | | $SP^3$ | >97 | 19 |
| TA-Ac-V2 | ECR8285 | $IDA^2$ | >97 | 18 |
| | | $SP^3$ | >97 | 20 |
| TA-Cv | ECR8285 | $IDA^1$ | >97 | 9 |
| | | $IDA^2$ | >97 | 12 |
| | | $SP^3$ | >97 | 13 |
| TA-Cv-V1 | ECR8285 | $SP^3$ | >97 | 21 |
| TA-Cv-V2 | ECR8285 | $SP^3$ | >97 | 24 |

IDA*-epoxy resin was modified by iminodiacitic-metal, it adsorbs and binds to the enzyme in affinity.
$IDA^1$-epoxy resin was modified by iminodiacitic, followed by PEI and metal, and treated with a cross-linking agent before addition of enzyme;
$IDA^2$-epoxy resin was modified by iminodiacitic, followed by PEI and metal, enzyme was added before a cross-linking agent;
$IDA^3$-epoxy resin was modified by iminodiacitic, followed by PEI and metal, and treated with a PEG-treated cross-linking agent before addition of enzyme;
$IDA^4$-epoxy resin was modified by iminodiacitic, followed by PEI and metal, enzyme was added before a PEG-treated cross-linking agent;
$SP^1$-epoxy resin was oxidized by sodium periodate, followed by PEI modification, and treated with a cross-linking agent before addition of enzyme
$SP^2$-epoxy resin was oxidized by Sodium periodate, followed by PEI modification, and treated with a cross-linking agent before addition of enzyme, extra the cross-linking agent was added at last;
$SP^3$-epoxy resin was oxidized by sodium periodate, followed by PEI modification, enzyme was added before a cross-linking agent;
$SP^4$-epoxy resin is oxidized by the sodium periodate, followed byPEI and metal, combined with the enzyme, and then further cross-linked with a PEG-treated cross-linking agent.

Embodiment 11

Conversion and Reusability Test of Immobilized Ketoreductase

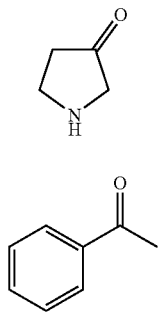

In a 10 mL reaction bulb, 0.5 mL of isopropanol (IPA) is added, 0.1 g of a main raw material 3 or 4 is dissolved, 0.5 mL of 0.1 M PB 7.0 and 1-10 mg of NAD+ are added, then 5 mg of enzyme powder or the immobilized enzyme prepared from 10 mg of the enzyme powder is added, it is stirred at 30° C. for 16-20 h. The conversion rate of the system is detected by a gas chromatography (GC), and reaction data is shown in Table 10 below:

TABLE 10

| Enzyme | Support | Support modification material | Conversion (%) | Cycles |
|---|---|---|---|---|
| KRED-Ac | Free enzyme | –/– | >99 | 1 |
|  | LX1000EA | IDA* | 60 | 2 |
|  |  | IDA$^1$ | 85 | 6 |
|  |  | IDA$^2$ | 85 | 5 |
|  |  | IDA$^4$ | 85 | 5 |
|  |  | SP$^2$ | 80 | 5 |
|  |  | SP$^3$ | 80 | 5 |
|  | ECR8285 | IDA* | 90 | 4 |
|  |  | IDA$^1$ | 90 | 8 |
|  |  | IDA$^2$ | 90 | 9 |
|  |  | IDA$^3$ | 85 | 11 |
|  |  | SP$^2$ | 85 | 8 |
|  |  | SP$^3$ | 80 | 10 |
|  | LX1000HFA | IDA* | 90 | 5 |
|  |  | IDA$^3$ | 90 | 11 |
|  |  | SP$^2$ | 90 | 12 |
|  | ES1 | IDA* | 90 | 3 |
|  |  | IDA$^1$ | 85 | 6 |
|  |  | IDA$^2$ | 85 | 6 |
|  |  | IDA$^4$ | 80 | 6 |
|  |  | SP$^2$ | 80 | 7 |
|  |  | SP$^3$ | 80 | 6 |
|  | ES105 | IDA* | 85 | 2 |
|  |  | IDA$^1$ | 85 | 5 |
|  |  | IDA$^2$ | 85 | 4 |
|  |  | IDA$^4$ | 80 | 6 |
|  |  | SP$^2$ | 80 | 5 |
|  |  | SP$^3$ | 80 | 5 |
| KRED-Ac-V1 | LX1000HFA | SP$^2$ | 90 | 15 |
| KRED-Ac-V2 | LX1000HFA | SP$^2$ | 90 | 18 |
| KRED-Am | Free enzyme | –/– | 90 | 1 |
|  | LX1000EP | IDA* | 70 | 5 |
|  |  | IDA$^1$ | 85 | 9 |
|  |  | IDA$^2$ | 85 | 13 |
|  |  | IDA$^4$ | 80 | 10 |
|  |  | SP$^2$ | 90 | 11 |
|  |  | SP$^3$ | 85 | 12 |

Embodiment 12

Conversion and Reusability Test of Immobilized CHMOs

The activity of the CHMO epoxy support immobilized enzyme is detected by performing a reaction on the following substrate 5:

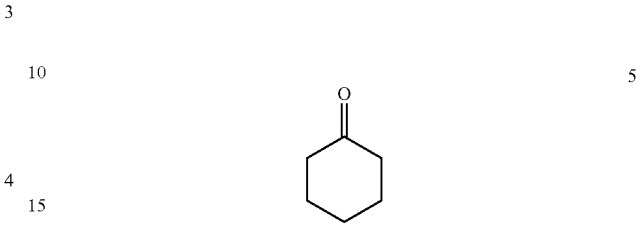

0.3 mL of isopropanol is loaded into a 10 mL reaction bulb, subsequently 100 mg of a substrate 5 is added, 3 mL of 0.1 M PB (pH 8.0) containing 5 mg of NADP+ is added, and then 2 mg of alcohol dehydrogenase ADH-Tb free enzyme and 20 mg of cyclohexanone monooxygenase free enzyme immobilized enzyme prepared from 50 mg of the free enzyme are added. It is reacted at 30° C. for 16-20 h to test the conversion rate. After each round of the reaction, the immobilized enzyme is separated and reused in the next round of the reaction, and the number of reuses is investigated. The conversion rate of the system is detected by GC, and reaction data is shown in Table 11 below:

TABLE 11

| Enzyme | Support | Support modification material | Conversion (%) | Cycles |
|---|---|---|---|---|
| CHMO-Bp | Free enzyme | –/– | >99 | 1 |
|  | HFA001 | IDA* | 60 | 4 |
|  |  | IDA$^1$ | 85 | 5 |
|  |  | IDA$^2$ | 85 | 7 |
|  |  | IDA$^4$ | 85 | 7 |
|  |  | SP$^2$ | 80 | 6 |
|  |  | SP$^4$ | 80 | 7 |
|  | LX1000HFA | IDA* | 90 | 6 |
|  |  | IDA$^1$ | 90 | 8 |
|  |  | IDA$^2$ | 90 | 8 |
|  |  | IDA$^4$ | 90 | 9 |
|  |  | SP$^2$ | 85 | 6 |
|  |  | SP$^3$ | 80 | 7 |
|  | ECR8209 | IDA$^1$ | 85 | 5 |
|  |  | IDA$^2$ | 85 | 7 |
|  |  | IDA$^4$ | 80 | 8 |
|  |  | SP$^2$ | 80 | 6 |
|  |  | SP$^4$ | 80 | 7 |
|  | LX103B | IDA* | 85 | 4 |
|  |  | IDA$^1$ | 85 | 6 |
|  |  | IDA$^4$ | 80 | 7 |
|  |  | SP$^3$ | 80 | 6 |
|  |  | SP$^4$ | 80 | 6 |
| CHMO-Bp-V1 |  |  |  |  |
| CHMO-Rr | Free enzyme | –/– | 90 | 1 |
|  | LX1000EP | IDA* | 70 | 5 |
|  |  | IDA$^1$ | 85 | 7 |
|  |  | IDA$^2$ | 85 | 9 |
|  |  | IDA$^4$ | 80 | 9 |
|  |  | SP$^2$ | 90 | 7 |
|  |  | SP$^3$ | 85 | 8 |
|  | EP200 | IDA$^2$ | 80 | 7 |
|  | LX1000HFA | IDA$^2$ | 90 | 10 |
|  | HFA001 | IDA$^2$ | 85 | 8 |
|  | LX103B | IDA$^2$ | 85 | 6 |
|  | LX107S | IDA$^2$ | 85 | 7 |
|  | LX1000SW | IDA$^2$ | 85 | 9 |
|  | ES1 | IDA$^2$ | 85 | 7 |

TABLE 11-continued

| Enzyme | Support | Support modification material | Conversion (%) | Cycles |
|---|---|---|---|---|
| CHMO-Rr-V1 | LX1000HFA | $IDA^2$ | 90 | 15 |
| CHMO-Rr-V2 | LX1000HFA | $IDA^2$ | 90 | 18 |
| CHMO-Rs | Free enzyme | -/- | 90 | 1 |
|  | LX1000HFA | $IDA^1$ | 85 | 8 |
|  |  | $IDA^4$ | 85 | 10 |
|  |  | $SP^1$ | 85 | 8 |
|  |  | $SP^3$ | 85 | 9 |
|  | LX1000SD | $IDA^2$ | 85 | 6 |
|  | ES105 | $IDA^2$ | 85 | 7 |
|  | ES108 | $IDA^2$ | 85 | 7 |
|  | ES109 | $IDA^2$ | 85 | 8 |
| CHMO-Rs-V1 | LX1000HFA | $IDA^4$ | 90 | 18 |
| CHMO-Rs-V2 | LX1000HFA | $IDA^4$ | 90 | 16 |

Embodiment 13

Conversion and Reusability Test of Immobilized ERED

The activity of the ERED epoxy support immobilized enzyme is detected by performing a reaction on the following substrate 6:

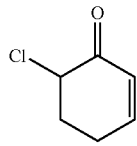

6

3 mL of 0.1 M PB (pH 7.0-8.0) is loaded into a 10 mL reaction bulb, subsequently 100 mg of a substrate 6 is added, then 10 mg of NAD(P)+, 80 mg of an ammonium formate, 2 mg of FDH, and 10 mg of a ERED free enzyme or immobilized enzyme prepared from 30 mg of the free enzyme are added. It is reacted at 30° C. for 16-20 h to test the conversion rate. After each round of the reaction, the immobilized enzyme is separated and reused in the next round of the reaction, and the number of reuses is investigated. The conversion rate of the system is detected by GC, and reaction data is shown in Table 12 below:

TABLE 12

| Enzyme | Support | Support modification material | Conversion (%) | Cycles |
|---|---|---|---|---|
| ERED-Sc | Free enzyme | -/- | >99 | 1 |
|  | LX1000HFA | IDA* | 99 | 6 |
|  |  | $IDA^1$ | 99 | 8 |
|  |  | $IDA^2$ | 99 | 9 |
|  |  | $IDA^4$ | 99 | 9 |
|  |  | $SP^2$ | 99 | 7 |
|  |  | $SP^3$ | 99 | 6 |
|  | HFA001 | IDA* | 99 | 4 |
|  |  | $IDA^1$ | 99 | 6 |
|  |  | $IDA^2$ | 99 | 7 |
|  |  | $IDA^4$ | 99 | 7 |
|  |  | $SP^2$ | 99 | 6 |
|  |  | $SP^3$ | 99 | 5 |
|  | ECR8285 | IDA* | 99 | 6 |
|  |  | $IDA^1$ | 99 | 9 |
|  |  | $IDA^2$ | 99 | 8 |
|  |  | $IDA^4$ | 99 | 8 |
|  |  | $SP^2$ | 99 | 7 |
|  |  | $SP^3$ | 99 | 6 |

TABLE 12-continued

| Enzyme | Support | Support modification material | Conversion (%) | Cycles |
|---|---|---|---|---|
| ERED-Chr | Free enzyme | -/- | 99 | 1 |
|  | LX1000EP | IDA* | 99 | 5 |
|  |  | $IDA^1$ | 99 | 9 |
|  |  | $IDA^2$ | 99 | 11 |
|  |  | $IDA^4$ | 99 | 8 |
|  |  | $SP^2$ | 99 | 8 |
|  | LX1000HFA | $IDA^1$ | 99 | 7 |
|  |  | $IDA^2$ | 99 | 9 |
|  |  | $SP^1$ | 99 | 8 |
|  |  | $SP^2$ | 99 | 9 |

Embodiment 14

Conversion and Reusability Test of Immobilized NITs

The activity of the NIT amino support immobilized enzyme is detected by performing a reaction on the following substrate 7:

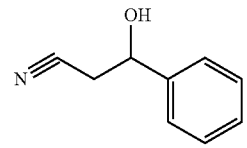

7

2 mL of 0.1 M PB (pH 7.0-8.0) is added to a 10 mL reaction bulb, and 100 mg of the above substrate 9 is added, then 20 mg of NIT free enzyme or the immobilized enzyme prepared from 30 mg of the free enzyme is added. After 16 h of the reaction at 30° C., the conversion rate is detected. After each round of the reaction, the immobilized enzyme is separated and reused in the next round of the reaction, and the number of reuses is investigated. The conversion rate of the system is detected by GC, and reaction data is shown in Table 13 below:

TABLE 13

| Enzyme | Support | Support modification material | Conversion (%) | Cycles |
|---|---|---|---|---|
| NIT-An | Free enzyme | -/- | >99 | 1 |
|  | LX1000HFA | IDA* | >99 | 6 |
|  |  | $IDA^2$ | >99 | 8 |
|  |  | $SP^3$ | >99 | 8 |
|  | LX1000EP | IDA* | >99 | 5 |
|  |  | $IDA^1$ | >99 | 8 |
|  |  | $SP^3$ | >99 | 7 |
|  | ECR8285 | IDA* | >99 | 6 |
|  |  | $IDA^2$ | >99 | 9 |
|  | ES103 | $IDA^2$ | >99 | 7 |
|  |  | $SP^3$ | >99 | 7 |
| NIT-Nc | Free enzyme | -/- | >99 | 1 |
|  | LX1000EP | IDA* | >99 | 8 |
|  |  | $IDA^2$ | >99 | 10 |
|  | LX1000HFA | $SP^2$ | >99 | 10 |
|  |  | $IDA^2$ | >99 | 11 |
|  | HFA001 | $IDA^2$ | >99 | 13 |
|  | ECR8285 | $IDA^2$ | >99 | 12 |
|  | LX103B | $IDA^2$ | >99 | 9 |
|  | ES1 | $IDA^2$ | >99 | 9 |

Embodiment 15

Conversion and Reusability Test of Immobilized IREDs, which are Detected by the Following Substrate 8.

2 mL of 0.1 M PB (pH 7.0-8.0) is added to a 10 mL reaction ball, and then 100 mg of the substrate 8, 10 mg of NAD+, 60 mg of an ammonium formate, 10 mg of FDH, and 10 mg of IRED free enzyme or immobilized enzyme prepared from 30 mg of the free enzyme are added. After 20 h of the reaction at 30° C., the conversion rate is detected. After each round of the reaction, the immobilized enzyme is separated and reused in the next round of the reaction, and the number of reuses is investigated.

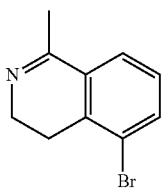

8

The conversion rate of the system is detected by HPLC, and reaction data is shown in Table 14 below:

TABLE 14

| Enzyme | Support | Support modification material | Conversion (%) | Cycles |
|---|---|---|---|---|
| IRED-Str | Free enzyme | -/- | >99 | 1 |
| | LX1000HFA | IDA* | >99 | 3 |
| | | IDA$^1$ | >99 | 6 |
| | | IDA$^2$ | >99 | 8 |
| | | SP$^2$ | >99 | 6 |
| | | SP$^3$ | >99 | 7 |
| | HFA001 | IDA$^2$ | >99 | 7 |
| | | SP$^2$ | >99 | 7 |
| | ECR8285 | IDA$^2$ | >99 | 8 |
| | | SP$^2$ | >99 | 7 |
| | | SP$^3$ | >99 | 7 |
| IRED-Bc | Free enzyme | -/- | >99 | 1 |
| | LX1000HFA | IDA* | >99 | 5 |
| | | IDA$^1$ | >99 | 8 |
| | | IDA$^2$ | >99 | 10 |
| | | SP$^2$ | >99 | 10 |
| | ES108 | IDA$^2$ | >99 | 8 |
| | LX1000SW | IDA$^2$ | >99 | 9 |
| | LX107S | IDA$^2$ | >99 | 8 |
| | EP200 | SP$^2$ | >99 | 9 |

Embodiment 16

Conversion and Reusability Test of Immobilized PAL

The activity and number of reuses of the immobilized enzyme are tested by performing a reaction on the following substrate 9:

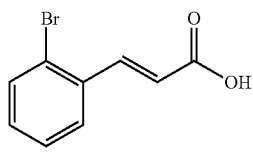

9

8 mL of 4 M ammonium carbamate aqueous solution (pH 9.0~9.5) is added into a 10 mL reaction bulb, and 100 mg of the above substrate 9 is added, then 10 mg of ammonia lyase free enzyme or immobilized enzyme prepared from 40 mg of the free enzyme is added. After 16-20 of the reaction at 30° C., the conversion rate is detected. After each round of the reaction, the immobilized enzyme is separated and reused in the next round of the reaction, and the number of reuses is investigated.

The conversion rate of the system is detected by HPLC, and reaction data is shown in Table 15 below:

TABLE 15

| Enzyme | Support | Support modification material | Conversion (%) | Cycles |
|---|---|---|---|---|
| PAL-An | Free enzyme | -/- | 80 | 1 |
| | LX1000HFA | IDA* | 80 | 4 |
| | | IDA$^2$ | 80 | 6 |
| | | SP$^3$ | 80 | 7 |
| | HFA001 | IDA* | 80 | 5 |
| | | IDA$^1$ | 80 | 8 |
| | | IDA$^2$ | 80 | 9 |
| | | IDA$^4$ | 80 | 9 |
| | | SP$^2$ | 80 | 8 |
| | | SP$^3$ | 80 | 9 |
| | ECR8285 | IDA* | 80 | 4 |
| | | IDA$^1$ | 80 | 7 |
| | | IDA$^2$ | 80 | 9 |
| | ES103 | IDA$^4$ | 80 | 8 |
| | | SP$^2$ | 80 | 8 |
| | | SP$^3$ | 80 | 7 |
| | | IDA$^2$ | 80 | 7 |
| | ES109 | IDA$^2$ | 80 | 6 |
| | EP200 | IDA$^2$ | 80 | 8 |
| | LX1000SW | IDA$^4$ | 80 | 7 |
| PAL-Ss | Free enzyme | -/- | 80 | 1 |
| | LX1000EP | IDA* | 80 | 6 |
| | | IDA$^2$ | 80 | 9 |
| | LX1000HFA | IDA$^2$ | 80 | 10 |
| | EP200 | IDA$^2$ | 80 | 8 |
| | ES108 | IDA$^2$ | 80 | 9 |

Embodiment 17

Conversion and Reusability Test of Immobilized AADH

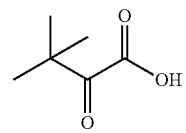

10

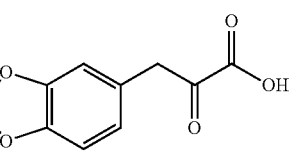

11

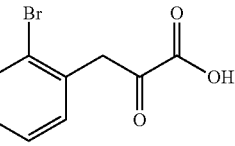

12

In a 10 mL reaction bulb, 5 mL of 0.1 M Tris-Cl buffer (pH 8.0-9.0) is added, 100 mg of a main raw material 10, a main raw material 11 or a main raw material 12 is added, 108 mg of ammonium chloride is added, and pH is adjusted to 7.5-8.0, then 10-50 mg of NAD$^+$, 150 mg of glucose, 5 mg of GDH, 10 mg of AADH or immobilized AADH prepared from 30 mg of the free enzyme are added. It is stirred at 30° C. for 16-20 h. The conversion rate of the system is detected by HPLC, and reaction data is shown in Table 16 below:

TABLE 16

| Enzyme | Support | Support modification material | Conversion (%) | Cycles |
|---|---|---|---|---|
| AADH-Bc | Free enzyme | –/– | >99 | 1 |
| | LX1000EP | IDA* | >99 | 5 |
| | | IDA$^1$ | >99 | 8 |
| | | IDA$^2$ | >99 | 8 |
| | | IDA$^4$ | >99 | 9 |
| | | SP$^2$ | >99 | 8 |
| | | SP$^3$ | >99 | 7 |
| | ECR8285 | IDA* | >99 | 5 |
| | | IDA$^1$ | >99 | 12 |
| | | IDA$^2$ | >99 | 10 |
| | | IDA$^4$ | >99 | 9 |
| | | SP$^2$ | >99 | 9 |
| | | SP$^3$ | >99 | 9 |
| | ECR8204 | IDA* | >99 | 5 |
| | | IDA$^1$ | >99 | 7 |
| | | IDA$^2$ | >99 | 6 |
| | | IDA$^4$ | >99 | 8 |
| | | SP$^2$ | >99 | 7 |
| | | SP$^3$ | >99 | 5 |
| | ES1 | IDA* | >99 | 7 |
| | | IDA$^1$ | >99 | 9 |
| | | IDA$^2$ | >99 | 9 |
| | | IDA$^4$ | >99 | 8 |
| | | SP$^2$ | >99 | 9 |
| | | SP$^3$ | >99 | 9 |
| AADH-Bs | Free enzyme | –/– | >99 | 1 |
| | ECR8285 | IDA* | 90 | 3 |
| | | IDA$^1$ | 90 | 5 |
| | | IDA$^2$ | 90 | 7 |
| | | IDA$^4$ | 90 | 8 |
| | | SP$^2$ | 80 | 7 |
| | | SP$^3$ | 85 | 6 |
| | LX1000EP | IDA* | 85 | 4 |
| | | IDA$^1$ | 90 | 9 |
| | | IDA$^2$ | 90 | 8 |
| | | IDA$^4$ | 6 | 6 |
| | | SP$^2$ | 80 | 6 |
| | | SP$^3$ | 90 | 8 |

Embodiment 18

Conversion and Reusability Test of Immobilized FDH

In a 10 mL reaction bulb, 5 mL of 0.1 M Tris-CI buffer (pH 8.0-9.0) is added, 100 mg of a main raw material 12 is dissolved, and 108 mg of ammonium chloride and 80 mg of ammonium fomate are added, pH is adjusted to 7.5-8.0, then 10-50 mg of NAD$^+$, 100 mg of AADH-Bc free enzyme, 5 mg of the FDH or the immobilized FDH prepared from 10 mg of the free enzyme are added. It is stirred at 30° C. for 16-20 h. The conversion rate of the system is detected by HPLC, and reaction data is shown in Table 17 below:

TABLE 17

| Enzyme | Support | Support modification material | Conversion (%) | Cycles |
|---|---|---|---|---|
| FDH | Free enzyme | –/– | >99 | 1 |
| | LX1000EP | No modification | <60 | 2 |
| | | IDA* | 85 | 3 |
| | | IDA$^1$ | >99 | 8 |
| | | IDA$^2$ | >99 | 8 |
| | | IDA$^4$ | >99 | 7 |
| | | SP$^2$ | >99 | 7 |
| | | SP$^3$ | >99 | 6 |

TABLE 17-continued

| Enzyme | Support | Support modification material | Conversion (%) | Cycles |
|---|---|---|---|---|
| | ECR8285 | No modification | <80 | 2 |
| | | IDA* | 85 | 4 |
| | | IDA$^1$ | >99 | 12 |
| | | IDA$^2$ | >99 | 13 |
| | | IDA$^4$ | >99 | 11 |
| | | SP$^2$ | >99 | 12 |
| | | SP$^3$ | >99 | 9 |
| | ECR8204 | IDA* | >99 | 2 |
| | | IDA$^1$ | >99 | 5 |
| | | IDA$^2$ | >99 | 5 |
| | | IDA$^4$ | >99 | 4 |
| | | SP$^2$ | >99 | 5 |
| | | SP$^3$ | >99 | 4 |
| | ECR8209 | IDA* | >99 | 2 |
| | | IDA$^1$ | >99 | 4 |
| | | IDA$^2$ | >99 | 4 |
| | | IDA$^4$ | >99 | 4 |
| | | SP$^2$ | >99 | 3 |
| | | SP$^3$ | >99 | 3 |
| | ES1 | IDA* | >99 | 3 |
| | | IDA$^1$ | >99 | 5 |
| | | IDA$^2$ | >99 | 5 |
| | | IDA$^4$ | >99 | 5 |
| | | SP$^2$ | >99 | 5 |
| | | SP$^3$ | >99 | 5 |
| | ES103 | IDA* | >99 | 2 |
| | | IDA$^1$ | >99 | 4 |
| | | IDA$^2$ | >99 | 3 |
| | | IDA$^4$ | >99 | 3 |
| | | SP$^2$ | >99 | 3 |
| | | SP$^3$ | >99 | 2 |

Embodiment 19

Use of Transferase Amino Support Immobilized Enzyme in Packed Bed Continuous Reaction The transaminase TA-Cv-V1 in the embodiment is immobilized on a support ECR8285, and immobilized by IDA$^1$. The obtained immobilized enzyme is filled into a columnar reactor with a column volume of 120 mL, and the amount of the immobilized enzyme is 72 g.

500 g of a substrate 1 is dissolved in 1.5 L of methanol, and 4 eq of isopropylamine hydrochloride (1.8 L of 6 M isopropylamine hydrochloride aqueous solution) and 5 g of PLP are added without PB (0.1 M, pH 8.0), and the volume is fixed to 5 L.

The flow rate is set to 0.6 mL/min, namely the retention time is 200 min, and the continuous reaction is performed. Effluent at an outlet is detected for the conversion rate. The conversion rate is >98%. After 260 h of the continuous operation, the conversion rate is not decreased. After 280 h of the operation, the conversion rate is decreased to 90%. It is specifically shown in Table 18.

TABLE 18

| Enzyme | Support | Amount of immobilized enzyme | Column volume | Retention time | Operation time | Conversion |
|---|---|---|---|---|---|---|
| TA-Cv-V1 | LX1000HA | 72 g | 120 mL | 200 min | 260 h | 97.5% |
| | | | | | 280 h | 90% |

Embodiment 20

Use of transferase immobilized enzyme in continuous stirred tank reaction

The same immobilized enzyme TA-Ac-V1 in Embodiment 1 is used, the support is LX1000HFA, and it is immobilized by a mode of $SP^2$. 50 g of the immobilized enzyme of the transaminase TA-Ac-V1 is added to a 200 mL reactor, and 150 mL of PB is added.

3.2 L of PB (0.1 M, pH 7.0), 1.8 L of isopropylamine hydrochloride aqueous solution (6 M) and 5 g of PLP are added to 500 g of a substrate 1, and it is prepared into a suspension by beating.

The substrate suspension is continuously added to a reaction bulb at a rate of 0.4 mL/min (namely the retention time is 500 min), and at the same time, the reaction system is extracted at an outlet at the same flow rate (a filter head is additionally installed at a tail end of a pipe, to prevent the immobilized enzyme from being extracted). Under this condition, the conversion rate may reach more than 90%, and the conversion rate is not decreased basically after 2000 h of the continuous operation. Results are shown in Table 19.

TABLE 19

| Enzyme | Support | Amount of immobilized enzyme | Column volume | Retention time | Operation time | Conversion |
|---|---|---|---|---|---|---|
| TA-Cv-V1 | ECR8409 | 50 g | 200 mL | 250 min | 200 h | >90% |
| | | | | | 210 h | 84% |

Embodiment 21

It is an ammonia lyase PAL-Ss immobilized enzyme, the support is HFA001, and it is immobilized by a mode of $IDA^4$. 6 g of the obtained immobilized enzyme is filled into a 10 mL columnar reactor.

500 g of a substrate 9 is dissolved in 4.5 L of ammonium carbamate aqueous solution (4 M, pH 9.0~9.5).

The flow rate is set to 0.03 mL/min, namely the retention time is 330 min, and the continuous reaction is performed. Effluent at an outlet is detected for the conversion rate, and the conversion rate is 80%. After 300 h of the continuous operation, the conversion rate is not decreased. After 310 h of the operation, the conversion rate is decreased to 70%. It is shown in Table 20.

TABLE 20

| Enzyme | Support | Amount of immobilized enzyme | Column volume | Retention time | Operation time | Conversion |
|---|---|---|---|---|---|---|
| PAL-Ss | LX1000EPN | 6 g | 10 mL | 100 min | 300 h | 80% |
| | | | | | 310 h | 70% |

Embodiment 22

It is the ketoreductase KRED-Ac-V1 immobilized enzyme prepared in the embodiment, the support is LX1000EP, and it is immobilized by a mode of $IDA^4$. 6 g of the obtained immobilized enzyme is filled into a 10 mL columnar reactor.

100 g of the substrate 3 is dissolved in 0.3 L of isopropanol, 0.7 L of PB (0.1 M, pH 7.0) is added for dissolution, and then 0.1 g of $NAD^+$ is added.

The flow rate is set to 0.05 mL/min, namely the retention time is 200 min, and the continuous reaction is performed. Effluent at an outlet is detected for the conversion rate. The conversion rate is >90%. After 200 h of the continuous operation, the conversion rate is not decreased. After 210 h of the operation, the conversion rate is decreased to 80%. It is shown in Table 21.

TABLE 21

Reaction results of KRED-AC immobilized enzyme in packed bed continuous reaction

| Enzyme | Support | Amount of immobilized enzyme | Column volume | Retention time | Operation time | Conversion |
|---|---|---|---|---|---|---|
| KRED-Ac-V | LX1000EP | 6 g | 10 mL | 100 min | 220 h | 90% |
| | | | | | 210 h | 80% |

Embodiment 23

Investigation of Various Parameters of Epoxy Resin Immobilization by Sodium Periodate Oxidation The concentration and amount of an acetic acid, the concentration and amount of a sodium periodate, and the concentration of a cross-linking agent are investigated.

FDH is immobilized on the LX1000HFA support by the method in Embodiment 4, the concentration of IDA is set to 0.2~3 mol/L, the volume/mass ratio of IDA solution and support is 2~25:1, the concentration of the metal ions is set to 5~100 mmol/L, and the range of the cross-linking agent dextran aldehyde (DA) is investigated. Herein, the IDA concentration of 1-2 mol/L is best, and it is best while the volume/mass ratio to the support is 10-20:1; the activity is better while the metal ion concentration is 10-100 mmol/L, in view of the cost, a concentration of 10~50 mmol/L may be used; and the cross-linking agent DA is best in the range of 0.5%~2%. The specific parameters and results are shown in Table 22.

TABLE 22

| Enzyme | Support | IDA concentration, mol/L | Ratio of IDA solution volume to support mass (v/m) | Metal ion concentration, mmol/L | Cross-linking agent and its concentration, % | Conversion, % | Number of reuses, times |
|---|---|---|---|---|---|---|---|
| FDH | LX1000HFA | 1 | 10 | 20 | 0.05 DA | 99 | 8 |
| | | 1 | 10 | 20 | 0.1 DA | 99 | 10 |
| | | 1 | 10 | 20 | 0.2 DA | 99 | 10 |
| | | 1 | 10 | 20 | 0.5 DA | 99 | 12 |
| | | 1 | 10 | 20 | 1 DA | 99 | 12 |
| | | 1 | 10 | 20 | 2 DA | 99 | 12 |
| | | 1 | 10 | 20 | 2.5 DA | 99 | 10 |
| | | 1 | 10 | 5 | 1 DA | 99 | 9 |
| | | 1 | 10 | 10 | 1 DA | 99 | 11 |
| | | 1 | 10 | 30 | 1 DA | 99 | 11 |
| | | 1 | 10 | 50 | 1 DA | 99 | 12 |
| | | 1 | 10 | 70 | 1 DA | 99 | 12 |
| | | 1 | 10 | 100 | 1 DA | 99 | 12 |
| | | 2 | 2 | 20 | 1 DA | 99 | 5 |
| | | 2 | 5 | 20 | 1 DA | 99 | 8 |
| | | 2 | 10 | 20 | 1 DA | 99 | 12 |
| | | 2 | 15 | 20 | 1 DA | 99 | 12 |
| | | 2 | 20 | 20 | 1 DA | 99 | 12 |
| | | 2 | 25 | 20 | 1 DA | 99 | 11 |
| | | 0.2 | 10 | 20 | 1 DA | 99 | 7 |
| | | 0.5 | 10 | 20 | 1 DA | 99 | 10 |
| | | 1 | 10 | 20 | 1 DA | 99 | 12 |
| | | 2 | 10 | 20 | 1 DA | 99 | 12 |
| | | 3 | 10 | 20 | 1 DA | 99 | 10 |

The acetic acid concentration, the volume/mass ratio of the acetic acid solution to the support, the concentration of sodium periodate, the volume/mass ratio of the sodium periodate solution to the support, and the concentration of the cross-linking agent GA are investigated.

By the same method in Embodiment 3, FDH is immobilized to the support HFA, the different acetic acid concentrations, volume/mass ratios of acetic acid solution to the support, concentrations of sodium periodate, volume/mass ratios of sodium periodate solution to the support, and concentrations of the cross-linking GA are set. Results show that the optimal concentration of the acetic acid is 1-2 mol/L; the optimal volume/mass ratio of the acetic acid solution to the support is 10~15:1; the optimal concentration of the sodium periodate is 0.1~0.2 mol/L, and the effects are all better while the volume-to-mass ratio of the support is 5~25, in view of cost saving, it may be 5~15:1 preferably; and it is better while the concentration of the cross-linking agent is 0.5%~2%. The specific parameters and results are shown in Table 23.

TABLE 23

| Enzyme | Support | Acetic acid concentration, mol/L | Ratio of acetic acid solution volume to support mass (v/m) | Sodium periodate concentration, mol/L | Ratio of sodium periodate solution volume to support mass (v/m) | Cross-linking agent and its concentration, % | Conversion, % | Number of reuses, times |
|---|---|---|---|---|---|---|---|---|
| FDH | HFA001 | 1 | 5 | 0.1 | 5 | 0.05 GA | 99 | 4 |
| | | 1 | 5 | 0.1 | 5 | 0.1 GA | 99 | 7 |
| | | 1 | 5 | 0.1 | 5 | 0.5 GA | 99 | 11 |
| | | 1 | 5 | 0.1 | 5 | 1 GA | 99 | 11 |
| | | 1 | 5 | 0.1 | 5 | 1.5 GA | 99 | 12 |
| | | 1 | 5 | 0.1 | 5 | 2 GA | 99 | 12 |
| | | 1 | 5 | 0.1 | 5 | 2.5 GA | 99 | 10 |
| | | 1 | 5 | 0.1 | 5 | 3 GA | 99 | 9 |
| | | 1 | 5 | 0.1 | 5 | 4 GA | 99 | 5 |
| | | 0.3 | 5 | 0.1 | 5 | 2 GA | 99 | 6 |
| | | 0.5 | 4 | 0.1 | 5 | 2 GA | 99 | 10 |
| | | 0.5 | 5 | 0.1 | 5 | 2 GA | 99 | 11 |
| | | 0.5 | 10 | 0.1 | 5 | 2 GA | 99 | 11 |
| | | 0.5 | 15 | 0.1 | 5 | 2 GA | 99 | 11 |
| | | 0.5 | 20 | 0.1 | 5 | 2 GA | 99 | 9 |
| | | 1 | 5 | 0.05 | 5 | 2 GA | 99 | 8 |
| | | 1 | 5 | 0.2 | 5 | 2 GA | 99 | 12 |

TABLE 23-continued

| Enzyme | Support | Acetic acid concentration, mol/L | Ratio of acetic acid solution volume to support mass (v/m) | Sodium periodate concentration, mol/L | Ratio of sodium periodate solution volume to support mass (v/m) | Cross-linking agent and its concentration, % | Conversion, % | Number of reuses, times |
|---|---|---|---|---|---|---|---|---|
| | | 1 | 5 | 0.3 | 5 | 2 GA | 99 | 12 |
| | | 1 | 5 | 0.5 | 5 | 2 GA | 99 | 12 |
| | | 1 | 5 | 0.7 | 5 | 2 GA | 99 | 6 |
| | | 1 | 5 | 0.1 | 3 | 2 GA | 99 | 6 |
| | | 1 | 5 | 0.1 | 10 | 2 GA | 99 | 11 |
| | | 1 | 5 | 0.1 | 15 | 2 GA | 99 | 12 |
| | | 1 | 5 | 0.1 | 20 | 2 GA | 99 | 12 |
| | | 1 | 5 | 0.1 | 25 | 2 GA | 99 | 12 |
| | | 2 | 5 | 0.1 | 5 | 2 GA | 99 | 11 |
| | | 3 | 5 | 0.1 | 5 | 2 GA | 99 | 8 |

Investigation of Amount of PEI

By the same methods in Embodiment 2 (IDA4) and Embodiment 5 (SP3), FDH is immobilized to the support ECR8285, PEIs with different molecular weights are selected, and different PEI concentrations are set, to investigate the appropriate amount of PEI, and investigate the effects of different pH values on the immobilized enzyme. Results show that the PEIs have the similar effects while the molecular weight is from 3 KDa to 70 KDa, and the optimal concentration range of PEI is 1%~2%; and while pH is 6.0~10.0, the effect on the immobilized enzyme activity is not large, while pH is 7~9, the stability is the best. The specific parameters and results are shown in Table 24.

TABLE 24

| Enzyme | Support | Method | PEI molecular weight | PEI concentration, % | PH | Conversion, % | Number of reuses, times |
|---|---|---|---|---|---|---|---|
| FDH | ECR8285 | IDA2 | 3 KDa | 0.5 | 7.0 | 99 | 9 |
| | | | | 1 | 7.0 | 99 | 12 |
| | | | | 2 | 7.0 | 99 | 11 |
| | | | | 3 | 7.0 | 99 | 10 |
| | | | | 4 | 7.0 | 99 | 7 |
| | | | 20 KDa | 0.2 | 7.0 | 99 | 7 |
| | | | | 0.5 | 7.0 | 99 | 12 |
| | | | | 2 | 7.0 | 99 | 11 |
| | | | | 3 | 7.0 | 99 | 9 |
| | | | | 4 | 7.0 | 99 | 6 |
| | | | 50 KDa | 1 | 7.0 | 99 | 13 |
| | | | | 2 | 7.0 | 99 | 11 |
| | | | 70 KDa | 0.5 | 7.0 | 99 | 12 |
| | | | | 1 | 6.0 | 99 | 5 |
| | | | | 1 | 6.5 | 99 | 7 |
| | | | | 1 | 7.0 | 99 | 11 |
| | | | | 1 | 8.0 | 99 | 11 |
| | | | | 1 | 9.0 | 99 | 11 |
| | | | | 1 | 10.0 | 99 | 10 |
| | | | | 1 | 11.0 | 80 | 2 |
| | | | | 2 | 7.0 | 99 | 11 |
| | | | | 3 | 7.0 | 99 | 8 |
| | | SP3 | 3 KDa | 0.5 | 7.0 | 99 | 7 |
| | | | | 1 | 7.0 | 99 | 10 |
| | | | | 1 | 9.0 | 99 | 10 |
| | | | | 1 | 11.0 | 80 | 3 |
| | | | | 2 | 7.0 | 99 | 11 |
| | | | 70 KDa | 0.5 | 7.0 | 99 | 10 |
| | | | | 1 | 7.0 | 99 | 12 |
| | | | | 1 | 8.0 | 99 | 12 |
| | | | | 1 | 10.0 | 99 | 10 |
| | | | | 1 | 11.0 | 80 | 3 |
| | | | | 2 | 7.0 | 99 | 11 |
| | | | | 3 | 8.0 | 99 | 9 |

Investigation of Proportion of PEG-Modified Cross-Linking Agent

By the same methods in Embodiment 7 (SP4) and Embodiment 9 (IDA4), FDH is immobilized on the support ECR8285, and the range of PEG and the ratio of PEG to GA in the methods of PEG-modified glutaraldehyde are investigated. Results show that PEG200, PEG2000 and PEG6000 may all modify the glutaraldehyde. While the ratio of PEG to GA is in the range of 1:1~10:1, the reusability of the enzyme is better, and is best while the ratio is 2:1~4:1. The specific parameters and results are shown in Table 25.

TABLE 25

| Enzyme | Support | Method | PEG and cross-linking proportion | Conversion, % | Number of re-uses, times |
|---|---|---|---|---|---|
| FDH | ECR8285 | IDA4 | PEG200:GA = 1:1 | 99 | 10 |
|  |  |  | PEG200:GA = 3:1 | 99 | 11 |
|  |  |  | PEG200:GA = 5:1 | 99 | 10 |
|  |  |  | PEG200:GA = 7:1 | 99 | 10 |
|  |  |  | PEG200:GA = 10:1 | 99 | 9 |
|  |  |  | PEG200:GA = 12:1 | 99 | 8 |
|  |  |  | PEG2000:GA = 3:1 | 99 | 11 |
|  |  |  | PEG2000:GA = 5:1 | 99 | 11 |
|  |  |  | PEG2000:GA = 7:1 | 99 | 10 |

TABLE 25-continued

| Enzyme | Support | Method | PEG and cross-linking proportion | Conversion, % | Number of re-uses, times |
|---|---|---|---|---|---|
|  |  |  | PEG2000:GA = 10:1 | 99 | 10 |
|  |  |  | PEG6000:GA = 3:1 | 99 | 12 |
|  |  |  | PEG6000:GA = 5:1 | 99 | 12 |
|  |  |  | PEG6000:GA = 7:1 | 99 | 11 |
|  |  | SP4 | PEG200:GA = 5:1 | 99 | 12 |
|  |  |  | PEG200:GA = 7:1 | 99 | 12 |
|  |  |  | PEG200:GA = 10:1 | 99 | 11 |
|  |  |  | PEG2000:GA = 3:1 | 99 | 13 |
|  |  |  | PEG2000:GA = 5:1 | 99 | 12 |
|  |  |  | PEG2000:GA = 7:1 | 99 | 11 |
|  |  |  | PEG2000:GA = 10:1 | 99 | 10 |
|  |  |  | PEG6000:GA = 3:1 | 99 | 13 |
|  |  |  | PEG6000:GA = 5:1 | 99 | 13 |
|  |  |  | PEG6000:GA = 7:1 | 99 | 10 |

The above are only preferred embodiments of the present disclosure, and are not intended to limit the present disclosure. For those skilled in the art, the present disclosure may have various modifications and changes. Any modifications, equivalent replacements, improvements and the like made within the spirit and principle of the present disclosure shall be included within a scope of protection of the present disclosure.

What is claimed is:

1. A preparation method for a modified epoxy resin immobilized enzyme, comprising the following steps: modifying an epoxy resin, adding a polyethyleneimine to a modified epoxy resin for further modification, and then adding an enzyme to be immobilized and a glutaraldehyde for immobilization, to obtain the modified epoxy resin immobilized enzyme;

wherein the step of modifying the epoxy resin comprises using a sodium periodate to oxidize the epoxy resin or using an iminodiacetic acid to react with the epoxy resin;

wherein while the step of modifying the epoxy resin is to use the sodium periodate to oxidize the epoxy resin, before the sodium periodate is added, an acetic acid is firstly used to treat the epoxy resin, and after the enzyme to be immobilized and the glutaraldehyde are added for immobilization, it further comprises a step of adding a cross-linking agent glutaraldehyde or dextran aldehyde for secondary cross-linking.

2. The preparation method according to claim 1, wherein while the step of modifying the epoxy resin is to use the iminodiacetic acid to react with the epoxy resin, after the polyethyleneimine is added to the modified epoxy resin for further modification, it further comprises a step of adding metal ion solution for treatment, and the enzyme to be immobilized has a his tag.

3. The preparation method according to claim 1, wherein the adding sequence of the enzyme to be immobilized and the glutaraldehyde is the enzyme to be immobilized and the glutaraldehyde, or the glutaraldehyde and the enzyme to be immobilized.

4. The preparation method according to claim 1, wherein in the step of adding the polyethyleneimine to the modified epoxy resin for further modification, it further comprises adding a cofactor, and the cofactor is a nicotinamide adenine dinucleotide (NAD+), a nicotinamide adenine dinucleotide phosphate (NADP+) or a pyridoxal phosphate (PLP).

5. The preparation method according to claim 4, wherein in the step of treating the epoxy resin with the acetic acid, the acetic acid used is acetic acid solution, and the concentration of the acetic acid in the acetic acid solution is 0.5~3 M.

6. The preparation method according to claim 5, wherein the treatment time after the acetic acid is mixed with the epoxy resin is 6~24 h.

7. The preparation method according to claim 1, wherein the enzyme to be immobilized is selected from one or more in a group consisting of a transaminase derived from Chromobacterium *violaceum* DSM30191, a transaminase derived from *Aspergillus fumigatus*, a transaminase derived from *Vibrio fluvialis* strain JS17, a ketoreductase derived from *Acetobacter* sp. CCTCC M209061, a ketoreductase derived from *Candida macedoniensis* AKU4588, a cyclohexanone monooxygenase derived from *Rhodococcus* sp. Phil, a cyclohexanone monooxygenase derived from *Brachymonas petroleovorans*, a monooxygenase derived from *Rhodococcus ruber*-SD1, an ammonia lyase derived from *photorhab-*

*dus luminescens*, an ammonia lyase derived from Solenostemon *scutellarioides*, an Ene reductase derived from *Saccharomyces cerevisiae*, an Ene reductase derived from ChrySEQbacterium sp. CA49, an imine reductase derived from *Streptomyces* sp or *Bacillus cereus*, a leucine dehydrogenase derived from *Bacillus cereus*, a phenylalanine dehydrogenase derived from *Bacillus sphaericus*, a nitrilase derived from *Aspergillus niger* CBS 513.88 or a nitrilase derived from *Neurospora crassa* OR74A.

8. A modified epoxy resin immobilized enzyme, wherein the immobilized enzyme is prepared by the preparation method according to claim 1.

9. The preparation method according to claim 2, wherein the metal ion solution is selected from one or more of a cobalt chloride, a cobalt sulfate, a nickel chloride, a copper sulfate, a ferrous chloride or a ferrous sulfate.

10. The preparation method according to claim 2, wherein the concentration of the metal ion solution is 5~100 mmol/L.

11. The preparation method according to claim 4, wherein the polyethyleneimine participates in the reaction in the form of polyethyleneimine aqueous solution, and the final concentration of the cofactor in the polyethyleneimine aqueous solution is 1~10 mg/mL.

12. The preparation method according to claim 4, wherein before the cross-linking agent glutaraldehyde or dextran aldehyde is used, it further comprises a step of modifying the cross-linking agent with a polyethylene glycol (PEG), and the PEG modification of the cross-linking agent glutaraldehyde or dextran aldehyde comprises dissolving the cross-linking agent with water, adding the PEG, and stirring at 20~30° C. for 1~6 h, wherein the PEG is selected from PEG400~PEG2000, and the mass ratio of PEG to the cross-linking agent is 1:1~10:1.

13. The preparation method according to claim 5, wherein in the step of oxidizing the epoxy resin with the sodium periodate, the concentration of the sodium periodate in sodium periodate solution used is 50~500 mM; and the volume-to-mass ratio of the sodium periodate solution to the epoxy resin is 5~20:1.

14. The preparation method according to claim 5, wherein the molecular weight of the polyethyleneimine is 3 KDa~70 KDa, and the concentration of the polyethyleneimine aqueous solution is 0.5%~3%; and pH of the polyethyleneimine aqueous solution is 6~11.

15. The preparation method according to claim 5, wherein the volume/mass final concentration of the cross-linking agent glutaraldehyde or dextran aldehyde is 0.1%~3.

16. The preparation method according to claim 5, wherein the mass ratio of the enzyme to the modified epoxy resin is 0.05~0.3:1.

17. The preparation method according to claim 5, wherein in the step of using the iminodiacetic acid to react with the epoxy resin, the iminodiacetic acid used is iminodiacetic acid aqueous solution, the concentration of the iminodiacetic acid aqueous solution is 0.5~3 M, and the volume-to-mass ratio of the iminodiacetic acid aqueous solution to the epoxy resin is 5~20:1; and pH of the iminodiacetic acid aqueous solution is 6.0~10.0.

18. The preparation method according to claim 6, wherein the reaction time after the sodium periodate solution is mixed with the epoxy resin is 1~6 h.

19. The preparation method according to claim 6, wherein the reaction time after the polyethyleneimine aqueous solution is mixed with the epoxy resin is 1~20 h.

20. The preparation method according to claim 7, the transaminase derived from Chromobacterium *violaceum* DSM30191 is a mutant having a sequence of SEQ ID NO: 2 or SEQ ID NO: 3; the transaminase derived from *Arthrobacter citreus* is a mutant having a sequence of SEQ ID NO: 5 or SEQ ID NO: 6; the ketoreductase derived from *Acetobacter* sp. CCTCC M209061 is a mutant having a sequence of SEQ ID NO: 8 or SEQ ID NO: 9; the cyclohexanone monooxygenase derived from *Rhodococcus* sp. Phil is a mutant having a sequence of SEQ ID NO: 11 or SEQ ID NO: 12; and the cyclohexanone monooxygenase derived from *Rhodococcus ruber*-SDI is a mutant having a sequence of SEQ ID NO: 14 or SEQ ID NO: 15.

\* \* \* \* \*